(12) United States Patent
Bryll et al.

(10) Patent No.: US 9,961,253 B2
(45) Date of Patent: May 1, 2018

(54) AUTOFOCUS SYSTEM FOR A HIGH SPEED PERIODICALLY MODULATED VARIABLE FOCAL LENGTH LENS

(71) Applicant: Mitutoyo Corporation, Kanagawa-ken (JP)

(72) Inventors: Robert Kamil Bryll, Bothell, WA (US); Mark Lawrence Delaney, Shoreline, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 0 days. days.

(21) Appl. No.: 15/394,194

(22) Filed: Dec. 29, 2016

(65) Prior Publication Data

US 2017/0324895 A1    Nov. 9, 2017

Related U.S. Application Data

(63) Continuation-in-part of application No. 15/145,682, filed on May 3, 2016.

(51) Int. Cl.
| | |
|---|---|
| *G01B 11/24* | (2006.01) |
| *H04N 5/232* | (2006.01) |
| *G06T 7/00* | (2017.01) |
| *H04N 5/225* | (2006.01) |
| *H04N 5/235* | (2006.01) |

(52) U.S. Cl.
CPC ....... *H04N 5/23212* (2013.01); *G06T 7/0004* (2013.01); *H04N 5/2254* (2013.01);
(Continued)

(58) Field of Classification Search
CPC ........... H04N 5/23212; H04N 5/23264; H04N 5/2353; G02F 2001/294; G02B 7/04
See application file for complete search history.

(56) References Cited

U.S. PATENT DOCUMENTS

| | | |
|---|---|---|
| 6,542,180 B1 | 4/2003 | Wasserman et al. |
| 7,324,682 B2 | 1/2008 | Wasserman |
| | (Continued) | |

OTHER PUBLICATIONS

Bryll et al., U.S. Appl. No. 14/854,624, filed Sep. 15, 2015, "Chromatic Aberration Correction in Imaging System Including Variable Focal Length Lens," 55 pages.
(Continued)

*Primary Examiner* — Kara E Geisel
*Assistant Examiner* — Maurice Smith
(74) *Attorney, Agent, or Firm* — Seed IP Law Group LLP

(57) ABSTRACT

A system for providing an automatically focused image comprises an imaging system including a high speed periodically modulated variable focal length (VFL) lens, a VFL lens controller, a VFL-projected light source, a focus determining portion, an exposure timing adjustment circuit, and an exposure strobe time controller. The focus determining portion comprises an optical detector that inputs reflected VFL-projected light that is projected to, and reflected from, a workpiece through the VFL lens, and provides a focus deviation signal. The exposure timing adjustment circuit provides an exposure timing adjustment signal based on the focus deviation signal, which indicates a time when the imaging system focus Z-height approximately coincides with the workpiece surface Z height. The exposure strobe time controller uses the exposure timing adjustment signal to adjust the image exposure time so the imaging system focus Z-height coincides with the workpiece surface Z height at the adjusted image exposure time.

20 Claims, 14 Drawing Sheets

(52) U.S. Cl.
CPC ......... *H04N 5/2256* (2013.01); *H04N 5/2353* (2013.01); *H04N 5/23216* (2013.01); *G06T 2207/30164* (2013.01)

(56) References Cited

U.S. PATENT DOCUMENTS

| | | |
|---|---|---|
| 7,454,053 B2 | 11/2008 | Bryll et al. |
| 7,728,961 B2 | 6/2010 | Watson |
| 8,111,905 B2 | 2/2012 | Campbell |
| 8,111,938 B2 | 2/2012 | Bryll et al. |
| 8,194,307 B2 | 6/2012 | Arnold et al. |
| 9,060,117 B2 | 6/2015 | Bryll et al. |
| 9,143,674 B2 | 9/2015 | Gladnick |
| 2014/0368726 A1 | 12/2014 | Gladnick |
| 2015/0145980 A1 | 5/2015 | Bryll |

OTHER PUBLICATIONS

Emtman et al., U.S. Appl. No. 15/360,671, filed Nov. 23, 2016, "Machine Vision Inspection System and Method for Obtaining an Image With an Extended Depth of Field," 77 pages.

Gladnick, U.S. Appl. No. 14/795,409, filed Jul. 9, 2015, "Adaptable Operating Frequency of a Variable Focal Length Lens in an Adjustable Magnification Optical System," 58 pages.

Huang et al., "Response Time Investigation Based on GaAs Position Sensitive Detector," The Seventh International Conference on Sensor Device Technologies and Applications, 2016, 2 pages.

Koukourakis et al., "Axial scanning in confocal microscopy employing adaptive lenses (CAL)," Optics Express, vol. 22(5), Mar. 10, 2014, 15 pages.

Mermillod-Blondin et al., "High-speed varifocal imaging with a tunable acoustic gradient index of refraction lens," Department of Mechanical and Aerospace Engineering, Princeton University, Optics Letters, vol. 33(18), Princeton, New Jersey, Sep. 15, 2008, 3 pages.

Mitutoyo Corporation & Micro Encoder Inc. "QVPAK® 3D CNC Vision Measuring Machine," User's Guide, Version 7, 2003, 329 pages.

TAG Optics Inc., "The Physics Behind TAG Opctics' Technology and the Mechanism of Action of Using Sounds to Shape Light," Application Notice 12001, Physics behind the TAG Technology, 6 pages.

Robert Kamil Bryll, U.S. Appl. No. 14/841,051, filed Aug. 31, 2015, "Multi-Level Image Focus Using a Tunable Lens in a Machine Vision Inspection System," 64 pages.

AUTOFOCUS SYSTEM FOR A HIGH SPEED PERIODICALLY MODULATED VARIABLE FOCAL LENGTH LENS

CROSS-REFERENCE TO RELATED APPLICATION(S)

This application is a continuation-in-part of U.S. patent application Ser. No. 15/145,682, entitled "PHASE DIFFERENCE CALIBRATION IN A VARIABLE FOCAL LENGTH LENS SYSTEM," filed on May 3, 2016, the disclosure of which is hereby incorporated herein by reference in its entirety.

BACKGROUND

Technical Field

This disclosure relates to precision metrology and, more particularly, to machine vision inspection systems and other optical systems in which a variable focal length lens may be utilized to periodically modulate a focus position.

Description of the Related Art

Precision machine vision inspection systems (or "vision systems" for short) may be used for precise measurements of objects and to inspect other object characteristics. Such systems may include a computer, camera, optical system, and a stage that moves to allow workpiece traversal. One exemplary system, characterized as a general-purpose "off-line" precision vision system, is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, which is hereby incorporated by reference in its entirety. This type of system uses a microscope-type optical system and moves the stage to provide inspection images of small or large workpieces at various magnifications.

In various applications, it is desirable to perform high speed measurements for high throughput in either stationary or non-stop moving inspection systems. With respect to well-focused inspection images and Z-height measurements (which are generally based on the "best focus" height determination), the inspection image acquisition rate and the rate at which the Z-height measurements can be performed may be limited by the rate of Z-height focus position adjustment or motion speed. Conventional machine vision inspection systems may utilize various types of measurement operations (e.g., points-from-focus operations, etc.) which require movement of the camera through a range of Z-height positions. In confocal systems, movement may similarly be required through a range of Z-height positions (e.g., to determine a position that results in maximum confocal brightness, etc.) In such systems, the speed at which the Z-height measurements can be performed may be limited by the motion of one or more physical components of the systems to provide the range of Z-height positions.

To overcome these motion constraints, variable focus lenses (VFLs) such as innovative electronically deformable lenses and/or tunable acoustic gradient lenses (TAG lenses) are able to be periodically modulated and change a focus position at a very high rate (e.g., 70 KHz or more, in the case of a TAG lens). However, automatically determining and adjusting their image focus position to a particular surface with high very accuracy, and at a rate commensurate with their potential rate of focus variation, has proved problematic. Improved systems and methods for automatically determining and adjusting the image focus position are needed for various high-speed variable focus lenses used for high-speed precision inspection operations.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

As outlined above, generally speaking, the known methods of autofocusing an imaging system including a high speed periodically modulated VFL lens at a particular workpiece surface, in order to image that particular surface and/or establish its particular Z-height, are slower than desired. Known methods are not ideally suited to take advantage of the characteristics of a high speed periodically modulated VFL lens, and in particular are a limiting factor in relation to the extremely high focusing rate that may potentially be provided when using a TAG lens.

Disclosed herein, and particularly with reference to FIGS. 8-14, are combinations of elements, principles and operations that may be used to solve the problems outlined above, in various implementations of a system that that is operable to provide an automatically focused image using an imaging system that includes a high speed periodically modulated VFL lens. The disclosed implementations are particularly advantageous for use in combination with a TAG lens.

In particular, a system is disclosed for providing an automatically focused image using an imaging system that includes a high speed periodically modulated variable focal length (VFL) lens, wherein the system comprises the imaging system, a VFL lens controller, a VFL-projected light source, a focus determining portion, an exposure timing adjustment circuit, and an exposure strobe time controller. The imaging system includes at least an objective lens configured to input image light arising from a workpiece surface, a VFL lens configured to receive image light transmitted by the objective lens, and a camera configured to receive light transmitted by the VFL lens. The VFL lens controller is configured to control the VFL lens to periodically modulate its optical power and thereby periodically modulate a focus position of the imaging system over a plurality of imaging system focus Z heights along a Z-height direction. The VFL-projected light source comprises a light source configured to provide VFL-projected light along a focus monitoring light path to a back side of the VFL lens and through the VFL lens and the objective lens to the workpiece surface. The focus determining portion comprises an optical detector configured to input reflected VFL-projected light that has been reflected from a workpiece surface region and back through the objective lens and back through the VFL lens and back along the focus monitoring light path, and to provide at least one optical detector signal that is responsive to a difference between a focus Z height of the VFL-projected light and a Z height of the workpiece surface region, wherein the VFL-projected light focus Z-height is indicative of the imaging system focus Z-height, and the focus determining portion outputs a least one focus deviation signal based on the at least one optical detector signal.

The exposure timing adjustment circuit inputs the focus deviation signal and determines an exposure timing adjustment signal related to a time when the imaging system focus Z-height approximately coincides with the workpiece surface region Z height, based on the focus deviation signal. The exposure strobe time controller controls an image exposure time of the imaging system relative to a phase time of the periodically modulated focus position, wherein the exposure strobe time controller is configured input the exposure timing adjustment signal and provide an adjusted image exposure time based on the exposure timing adjustment signal, wherein the imaging system focus Z-height approximately coincides with the workpiece surface region Z height at the adjusted image exposure time.

DETAILED DESCRIPTION

Figure 1:
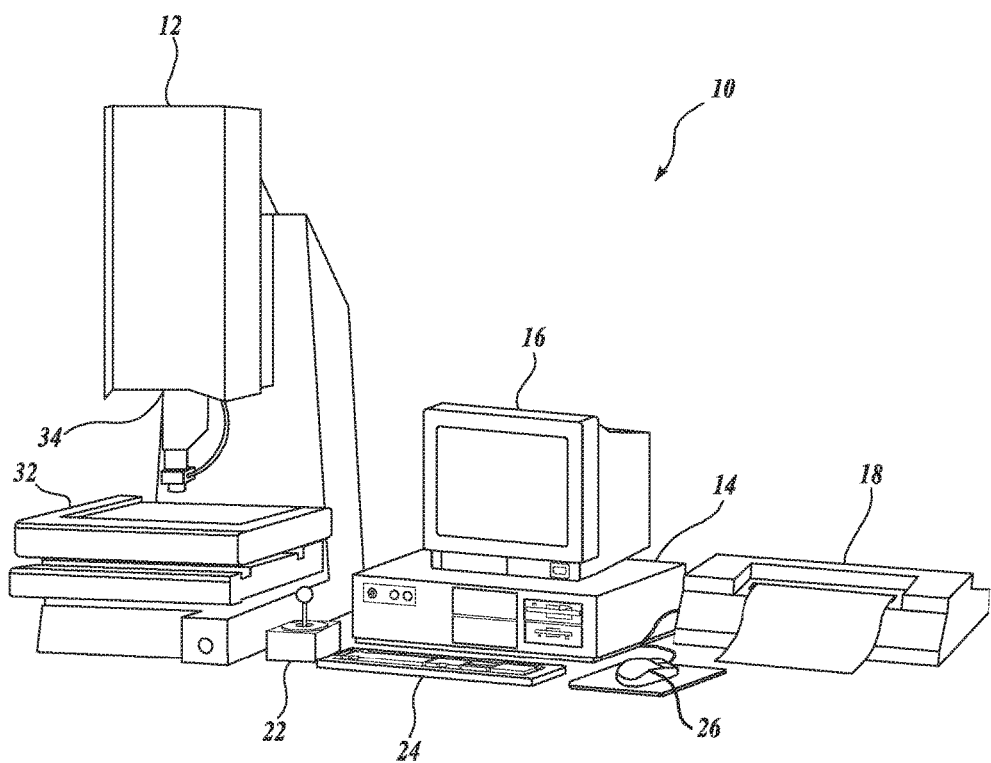
FIG. 1 is a diagram showing various typical components of a general-purpose precision machine vision inspection system.

FIG. 1 is a block diagram of one exemplary machine vision inspection system 10 usable in accordance with principles disclosed herein. The machine vision inspection system 10 includes a vision measuring machine 12 that is operably connected to exchange data and control signals with a controlling computer system 14, and with a monitor or display 16, printer 18, joystick 22, keyboard 24, and mouse 26. The monitor or display 16 may display a user interface suitable for controlling and/or programming the machine vision inspection system 10. In various implementations, a touchscreen tablet or the like may be substituted for and/or redundantly provide the functions of any or all of the computer system 14, display 16, joystick 22, keyboard 24, and mouse 26.

More generally, the controlling computer system 14 may comprise or consist of any computing system or device, and/or distributed computing environment, and the like, any of which may include one or more processors that execute software to perform the functions described herein. Processors include programmable general-purpose or special-purpose microprocessors, programmable controllers, application-specific integrated circuits (ASICs), programmable logic devices (PLDs), or the like, or a combination of such devices. Software may be stored in memory, such as random-access memory (RAM), read-only memory (ROM), flash memory, or the like, or a combination of such components. Software may also be stored in one or more storage devices, such as optical-based disks, flash memory devices, or any other type of non-volatile storage medium for storing data. Software may include one or more program modules that include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision measuring machine 12 includes a moveable workpiece stage 32 and an optical imaging system 34 that may include a zoom lens or interchangeable lenses. The zoom lens or interchangeable lenses generally provide various magnifications (e.g., 0.5× to 100×) for the images provided by the optical imaging system 34. Similar machine vision inspection systems are described in commonly assigned U.S. Pat. Nos. 7,324,682; 7,454,053; 8,111,905; and 8,111,938, each of which is hereby incorporated herein by reference in its entirety.

Figure 2:
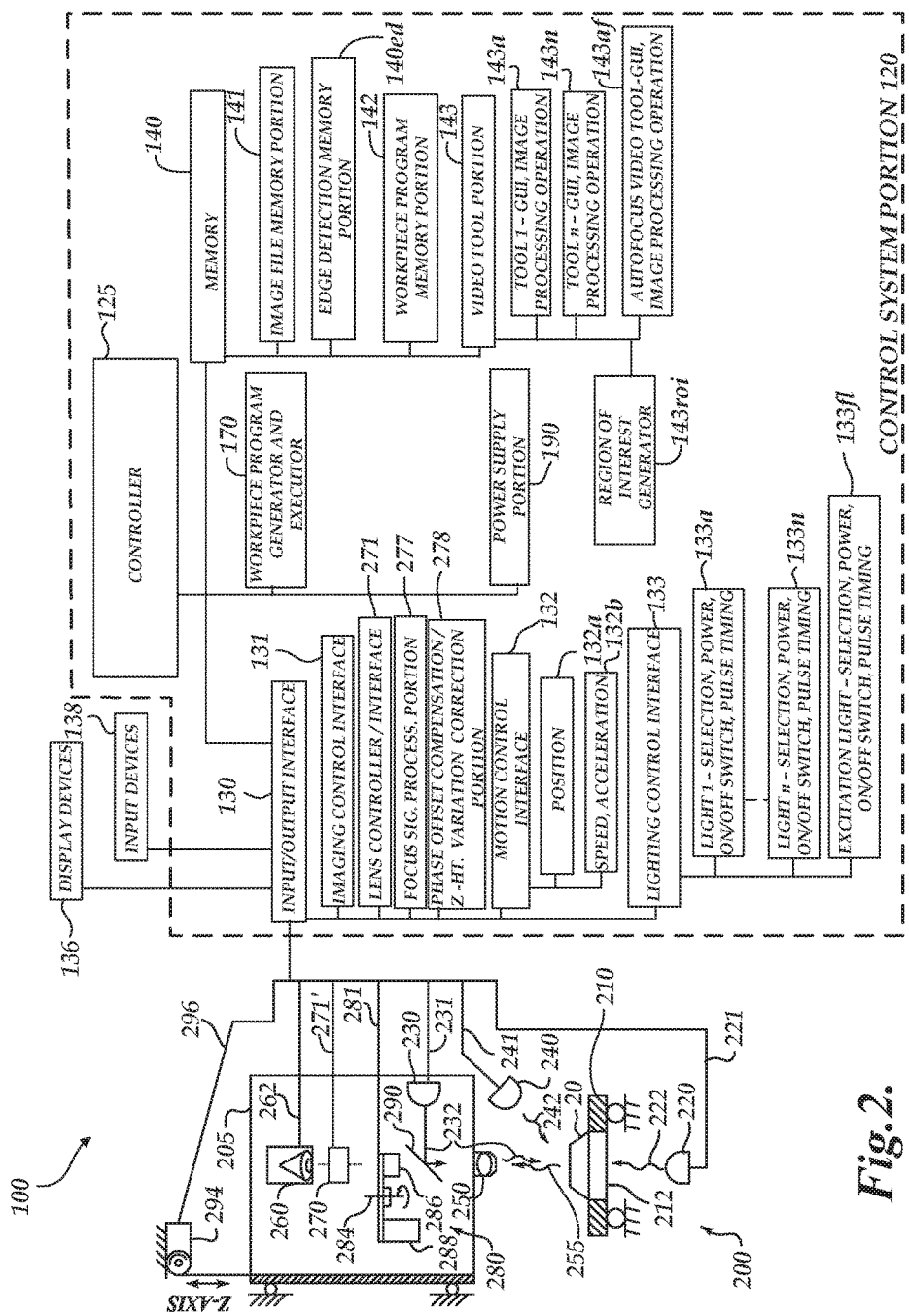
FIG. 2 is a block diagram of a control system portion and a vision components portion of a machine vision inspection system similar to that of FIG. 1 and including features disclosed herein.

FIG. 2 is a block diagram of a control system portion 120 and a vision components portion 200 of a machine vision inspection system 100 similar to the machine vision inspection system of FIG. 1, and including features as described herein. As will be described in more detail below, the control system portion 120 is utilized to control the vision components portion 200. The vision components portion 200 includes an optical assembly portion 205, light sources 220, 230, and 240, and a workpiece stage 210 that may have a central transparent portion 212. The workpiece stage 210 is controllably movable along x- and y-axes that lie in a plane that is generally parallel to the surface of the stage where a workpiece 20 may be positioned.

The optical assembly portion 205 may include an optical detector 260 (e.g., a camera, a confocal optical detector, etc.), a variable focal length (VFL) lens 270, and may also include an interchangeable objective lens 250 and a turret lens assembly 280 having lenses 286 and 288. Alternatively to the turret lens assembly, a fixed or manually interchangeable magnification-altering lens, or a zoom lens configuration, or the like, may be included. In various implementations, the various lenses may be included as part of a variable magnification lens portion of the optical assembly portion 205. In various implementations, the interchangeable objective lens 250 may be selected from a set of fixed magnification objective lenses (e.g., a set ranging from 0.5× to 100×, etc.)

In various implementations, the optical assembly portion 205 is controllably movable along a z-axis that is generally orthogonal to the x- and y-axes by using a controllable motor 294 that drives an actuator to move the optical assembly portion 205 along the z-axis to change the focus of the image of the workpiece 20. The controllable motor 294 is connected to an input/output interface 130 via a signal line 296. As will be described in more detail below, the VFL lens 270 may also be operated to periodically modulate a focus position. A workpiece 20, or a tray or fixture holding a plurality of workpieces 20, which is to be imaged using the machine vision inspection system 100 is placed on the workpiece stage 210. In various implementations, the workpiece stage 210 may be controllable to move (e.g., in the x- and y-axes directions) relative to the optical assembly portion 205, such that the imaged area (e.g., as imaged through the interchangeable objective lens 250, etc.) moves between locations on a workpiece 20, and/or among a plurality of workpieces 20.

One or more of a stage light 220, a coaxial light 230, and a surface light 240 (e.g., a ring light) may emit source light 222, 232, and/or 242, respectively, to illuminate the workpiece or workpieces 20. The coaxial light 230 may emit light 232 along a path including a mirror 290. The source light is reflected or transmitted as workpiece light 255, and the workpiece light (e.g., as used for imaging) passes through the interchangeable objective lens 250, the turret lens assembly 280, and the VFL lens 270, and is gathered by the optical detector 260 (e.g., a camera, a confocal optical detector, etc.) In various implementations, the optical detector 260 inputs the workpiece light and outputs signal data (e.g., one or more images of the workpiece(s) 20, a confocal brightness signal, etc.) on a signal line 262 to the control system portion 120. The light sources 220, 230, and 240 may be connected to the control system portion 120 through signal lines or busses 221, 231, and 241, respectively. The control system portion 120 may rotate the turret lens assembly 280 along axis 284 to select a turret lens through a signal line or bus 281 to alter an image magnification.

As shown in FIG. 2, in various exemplary implementations, the control system portion 120 includes a controller 125, the input/output interface 130, a memory 140, a workpiece program generator and executor 170, and a power supply portion 190. Each of these components, as well as the additional components described below, may be interconnected by one or more data/control busses and/or application programming interfaces, or by direct connections between the various elements. The input/output interface 130 includes an imaging control interface 131, a motion control interface 132, and a lighting control interface 133. The motion control interface 132 may include a position control element 132a, and a speed/acceleration control element 132b, although such elements may be merged and/or indistinguishable. The lighting control interface 133 may include lighting control elements 133a, 133n, and 133fl that control, for example, the selection, power, on/off switch, and strobe pulse timing, if applicable, for the various corresponding light sources of the machine vision inspection system 100.

In accordance with the principles disclosed herein, the input/output interface 130 may further include a lens controller/interface 271, a focus signal processing portion 277 and a phase offset compensation/Z-height variation correction portion 278, as will be described in more detail below with respect to FIGS. 3-7. Briefly, in one implementation, the lens controller/interface 271 may include a lens controller including a lens focus operating circuit and/or routine, or the like. The lens controller/interface 271 may be configured or controlled by a user and/or an operating program, and may utilize the signal line 271' to control the VFL lens 270 to periodically modulate its optical power (e.g., sinusoidally) and thereby periodically modulate a focus position of the imaging system over a plurality of focus positions along a Z-height direction at a determined operating frequency. In various implementations, the focus signal processing portion 277 may be configured to determine raw phase timing signal values corresponding to when signal data from the optical detector 260 (e.g., a camera system, a confocal optical detector, etc.) indicates that an imaged surface region (e.g., of the workpiece 20) is at a focus position. As will be described in more detail below, the phase offset compensating portion 278 may be configured to input raw phase timing signal values corresponding to imaged surface regions and perform a phase offset compensating process that provides Z-height measurements of the imaged surface regions, wherein at least one of Z-height errors or Z-height variations that are related to a phase offset contribution are at least partially eliminated.

In various implementations, the imaging control interface 131 and/or lens controller/interface 271 may further include an extended depth of field mode, as described in more detail in copending and commonly assigned U.S. Patent Publication No. 2015/0145980, which is hereby incorporated herein by reference in its entirety. An extended depth of field mode may be selected by a user to provide at least one image (e.g., a composite image) of a workpiece with a depth of field that is greater than what may be provided by the vision components portion 200 when focused at a single focus position. In various implementations, the imaging control interface 131 and/or lens controller/interface 271 may also further include a magnification change adjustment mode, which may be selected or automatically implemented when a magnification change is made or detected, as described in more detail in copending and commonly assigned U.S. patent application Ser. No. 14/795,409, entitled "Adaptable Operating Frequency of a Variable Focal Length Lens in an Adjustable Magnification Optical System", filed on Jul. 9, 2015, which is hereby incorporated herein by reference in its entirety. Other systems and methods including VFL lenses are described in copending and commonly assigned U.S. patent application Ser. No. 14/841,051, entitled "Multi-Level Image Focus Using a Tunable Lens in a Machine Vision Inspection System", filed on Aug. 31, 2015, and in copending and commonly assigned U.S. patent application Ser. No. 14/854,624, entitled "Chromatic Aberration Correction in Imaging System Including Variable Focal Length Lens", filed on Sep. 15, 2015, each of which is hereby incorporated herein by reference in its entirety.

The memory 140 may include an image file memory portion 141, an edge-detection memory portion 140ed, a workpiece program memory portion 142 that may include one or more part programs, or the like, and a video tool portion 143. The video tool portion 143 includes video tool portion 143a and other video tool portions (e.g., 143n) that determine the GUI, image-processing operation, etc., for each of the corresponding video tools, and a region of interest (ROI) generator 143roi that supports automatic, semi-automatic, and/or manual operations that define various ROIs that are operable in various video tools included in the video tool portion 143. The video tool portion also includes an autofocus video tool 143af that determines the GUI, image-processing operation, etc., for focus height measurement operations. The autofocus video tool 143af may additionally include a high-speed focus height tool that may be utilized to measure focus heights with high speed, as described in more detail in copending and commonly assigned U.S. Patent Publication No. 2014/0368726, which is hereby incorporated herein by reference in its entirety. In various implementations, the phase offset compensation/Z-height variation correction portion 278 and other related elements may be utilized in conjunction with, or otherwise included in, one or more of the video tools (e.g., the autofocus video tool 143af, a separate video tool, etc.)

In the context of this disclosure, and as is known by one of ordinary skill in the art, the term "video tool" generally refers to a relatively complex set of automatic or programmed operations that a machine vision user can implement through a relatively simple user interface (e.g., a graphical user interface, editable parameter windows, menus, and the like), without creating the step-by-step sequence of operations included in the video tool or resorting to a generalized text-based programming language, or the like. For example, a video tool may include a complex pre-programmed set of image-processing operations and computations that are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest (ROI) indicator through simple "handle dragging" operations using a mouse, in order to define the location parameters of a subset of an image that is to be analyzed by the image-processing operations of a particular instance of a video tool. It should be noted that the visible user interface features are sometimes referred to as the video tool with the underlying operations being included implicitly.

The signal lines or busses 221, 231, and 241 of the stage light 220, the coaxial light 230, and the surface light 240, respectively, are all connected to the input/output interface 130. The signal line 262 from the optical detector 260, the signal line 271' from the VFL lens 270, and the signal line 296 from the controllable motor 294 are connected to the input/output interface 130. In addition to carrying image data, the signal line 262 may carry a signal from the controller 125 that initiates certain processes (e.g., image acquisition, confocal brightness measurement, etc.).

One or more display devices 136 (e.g., the display 16 of FIG. 1) and one or more input devices 138 (e.g., the joystick 22, keyboard 24, and mouse 26 of FIG. 1) may also be connected to the input/output interface 130. The display devices 136 and input devices 138 may be used to display a user interface that may include various graphical user interface (GUI) features that are usable to perform inspection operations, and/or to create and/or modify part programs, to view the images captured by the optical detector 260, and/or to directly control the vision system components portion 200. The display devices 136 may display user interface features (e.g., as associated with the lens controller/interface 271, the focus signal processing portion 277, the phase offset compensation/Z-height variation correction portion 278, etc.)

In various exemplary implementations, when a user utilizes the machine vision inspection system 100 to create a part program for the workpiece 20, the user generates part program instructions by operating the machine vision inspection system 100 in a learn mode to provide a desired image-acquisition training sequence. For example, a training sequence may comprise positioning a particular workpiece feature of a representative workpiece in the field of view (FOV), setting light levels, focusing or autofocusing, acquiring an image, and providing an inspection training sequence applied to the image (e.g., using an instance of one or more of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and cause inspection operations to automatically inspect that particular workpiece feature (that is the corresponding feature in the corresponding location) on a current workpiece (e.g., a run mode workpiece), or workpieces, which is similar to the representative workpiece used when creating the part program.

Figure 3:
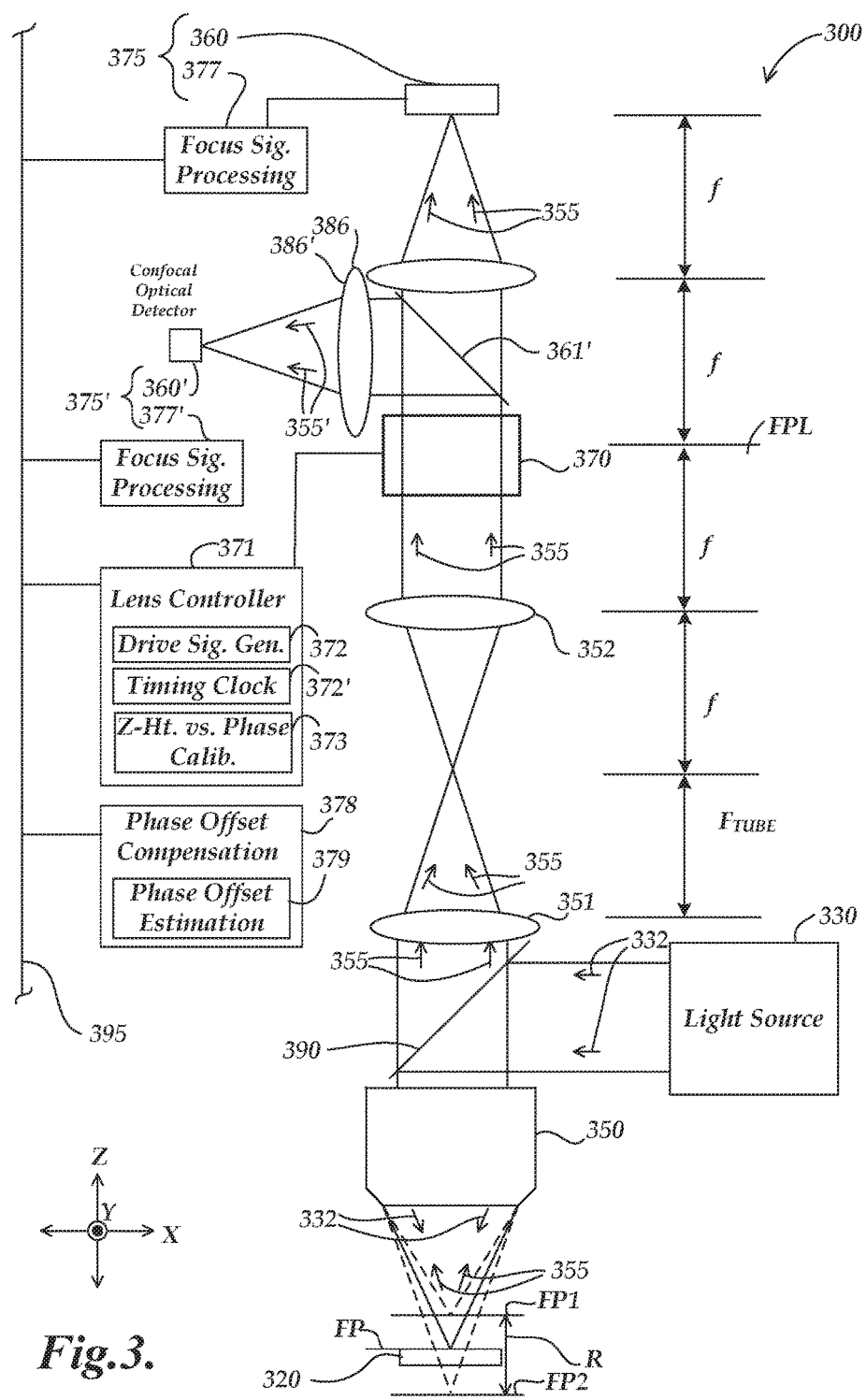
FIG. 3 is a schematic diagram of a variable focal length lens system that may be operated according to principles disclosed herein.

FIG. 3 is a schematic diagram of a VFL lens system 300 that may be adapted to a machine vision inspection system and operated according to the principles disclosed herein. It will be appreciated that certain numbered components 3XX of FIG. 3 may correspond to and/or have similar operations as similarly numbered components 2XX of FIG. 2, except as otherwise described below. As shown in FIG. 3, the VFL lens system 300 includes a light source 330, an objective lens 350, a tube lens 351, a relay lens 352, a VFL lens 370, a relay lens 386, a lens controller 371, a focus determining portion 375 and a phase offset compensating portion 378. In various implementations, each of the lens controller 371, focus determining portion 375 and/or phase offset compensating portion 378, as well as additional components, may be interconnected by one or more data/control busses (e.g., a system signal and control bus 395) and/or application programming interfaces, or by direct connections between the various elements.

In various implementations, the light source 330 is configurable to illuminate a workpiece 320 (e.g., with strobed or continuous-wave illumination) in a field of view of the VFL lens system 300. In various implementations, the light source 330 may include first, second, third, etc. sources of illumination as part of an illumination system. For example, the light source 330 may be operated to provide an instance of strobed illumination by operating a corresponding source of illumination (e.g., a source of illumination that is part of the light source 330). In various implementations, in order to achieve proper lighting balance, the light source 330 may be controllable so as to allow for independent adjustment of the intensity of all instances of strobed illumination (e.g., each corresponding to a different source of illumination within the light source 330) as well as simultaneous adjustment to control an overall brightness of an image.

In operation, in the implementation shown in FIG. 3, the light source 330 is a "coaxial" light source configured to emit source light 332 along a path including a partial mirror 390 and through the objective lens 350 to a surface of a workpiece 320, wherein the objective lens 350 receives workpiece light 355 that is focused at a focus position FP proximate to the workpiece 320, and outputs the workpiece light 355 to the tube lens 351. In other implementations, analogous light sources may illuminate the field of view in a non-coaxial manner, for example a ring light source may illuminate the field of view. In various implementations, the objective lens 350 may be an interchangeable objective lens and the tube lens 351 may be included as part of a turret lens assembly (e.g., similar to the interchangeable objective lens 250 and the turret lens assembly 280 of FIG. 2). In various implementations, the objective lens 350, tube lens 351, or any of the other lenses referenced herein may be formed from or operate in conjunction with individual lenses, compound lenses, etc. The tube lens 351 receives the workpiece light 355 and outputs it to the relay lens 352.

The relay lens 352 receives the workpiece light 355 and outputs it to the VFL lens 370. The VFL lens 370 receives the workpiece light 355 and outputs it to the relay lens 386. The relay lens 386 receives the workpiece light 355 and outputs it to an optical detector 360 (e.g., a camera, a confocal optical detector, etc.) of the focus determining portion 375. In various implementations, the optical detector 360 may capture an image of the workpiece 320 during an image exposure period, and may provide the image to a control system portion (e.g., similar to the operation of the optical detector 260 for providing an image to the control system portion 120 in FIG. 2).

In various implementations, the VFL lens system 300 may also, or alternatively, include an optional beamsplitter 361', an optional tube lens 386' and an optional focus determining portion 375'. The optional focus determining portion 375' may include an optional optical detector 360' and an optional focus signal processing portion 377'. In operation, the beamsplitter 361' may be configured to split the workpiece light 355 and output workpiece light 355' to the tube lens 386'. The tube lens 386' may be configured to output the workpiece light 355' to the optical detector 360'. In one implementation, the optical detector 360' may include a confocal optical detector, which may be configured to operate according to confocal principles, as will be understood by one skilled in the art.

As will be described in more detail below, in various implementations, the optical detector 360 (or 360') may be configured to input light from the imaging system including the VFL lens 370, and the focus signal processing portion 377 (or '377) may be configured to determine raw phase timing signal values corresponding to when signal data from the optical detector indicates that an imaged surface region (e.g., of the workpiece 320) is at a focus position. For example, in an implementation where the optical detector 360 is a camera, the signal data may correspond to one or more images acquired by the camera (e.g., an image stack), wherein contrast determinations such as points-from-focus operations or other analysis may be performed to determine when an imaged surface region of the workpiece 320 is at a focus position. Exemplary techniques for the determination and analysis of image stacks and focus curves, and for points-from-focus operations, are taught in U.S. Pat. Nos. 6,542,180 and 9,060,117, each of which is commonly assigned and hereby incorporated herein by reference in its entirety. As another example, in an implementation where the optical detector 360' is a confocal optical detector that is included as part of a confocal configuration, the signal data may correspond to a sensed level of confocal brightness. In such an implementation, the confocal optical detector 360' may be utilized during the periodic modulation of the optical power of the VFL lens 370 to determine when a maximum confocal brightness occurs, as corresponding to a focus position and as indicating a corresponding Z-height of an imaged surface region of the workpiece 320.

In an implementation where the VFL lens system 300 includes the focus determining portion 375' with the focus signal processing portion 377' and the optical detector 360' (e.g., a confocal optical detector), the optical detector 360 (e.g., a camera) may not need to be utilized for focus position determination. More specifically, in such an implementation, the optical detector 360' may be utilized for the focus determining functions, while the camera 360 may be utilized for imaging (e.g., and the focus signal processing portion 377 in some instances may not need to be included). Conversely, if the VFL lens system 300 does not include the focus determining portion 375' and only includes the focus determining portion 375, the camera 360 may be utilized for the focusing functions. As another alternative, in various implementations the VFL lens system 300 may include only the focus determining portion 375' with a confocal optical detector 360', and may not include the focus determining portion 375 with the camera 360 (e.g., when the VFL lens system 300 is included as part of a stand-alone confocal instrument, etc.)

The VFL lens 370 is electronically controllable to vary the focus position FP of the imaging system (e.g., during one or more image exposures, during a confocal brightness determination, etc.) The focus position FP may be moved within a range R bound by a focus position FP1 and a focus position FP2. It will be appreciated that in various implementations, the range R may be selected by a user or may result from design parameters or may otherwise be automatically determined. In general with respect to the example of FIG. 3, it will be appreciated that certain of the illustrated dimensions may not be to scale. For example, the VFL lens 370 may have different proportional dimensions than those illustrated (e.g., may be less wide and up to 50 mm long or longer for certain applications in order to provide a desired amount of lensing power, etc.)

In various implementations, a machine vision inspection system may comprise a control system (e.g., the control system 120 of FIG. 2) that is configurable to operate in conjunction with a lens controller 371 or to otherwise control the VFL lens 370 to periodically modulate a focus position of the VFL lens system 300. In some implementations, the VFL lens 370 may very rapidly adjust or modulate the focus position (e.g., periodically, at a rate of at least 300 Hz, or 3 kHz, or 70 kHz, or much higher). In one example implementation, the range R may be approximately 10 mm (e.g., for a 1× objective lens 350). In various implementations, the VFL lens 370 is advantageously chosen such that it does not require any macroscopic mechanical adjustments in the imaging system and/or adjustment of the distance between the objective lens 350 and the workpiece 320 in order to change the focus position FP. In such a case, as described in the previously incorporated '980 publication, an extended depth of field image may be acquired. Furthermore there are no macroscopic adjustment elements or associated positioning non-repeatability to degrade accuracy when the same imaging system is used for acquiring fixed focus inspection images, which may be used for precision measurements (e.g., for accuracies on the order of a few micrometers, or tenths of micrometers, or less, and the like). As described in the previously incorporated '726 publication, the changes in the focus position FP may also be utilized to rapidly acquire an image stack including a plurality of images at a plurality of positions along a Z-height direction proximate to the workpiece 320.

In various implementations, the VFL lens 370 may be a tunable acoustic gradient index of refraction ("TAG") lens. A tunable acoustic gradient index of refraction lens is a high-speed VFL lens that uses sound waves in a fluid medium to modulate a focus position and may periodically sweep a range of focal lengths at a frequency of several hundred kHz. Such a lens may be understood by the teachings of the article, "High-speed varifocal imaging with a tunable acoustic gradient index of refraction lens" (Optics Letters, Vol. 33, No. 18, Sep. 15, 2008), which is hereby incorporated herein by reference in its entirety. Tunable acoustic gradient index lenses and related controllable signal generators are available, for example from TAG Optics, Inc., of Princeton, N.J. The Model TL2.B.xxx series lenses, for example, are capable of modulation up to approximately 600 KHz.

In various implementations, as described in more detail in the previously incorporated '726 publication, the optical detector 360 may comprise a sensor with a global shutter, i.e., a sensor, that exposes each pixel simultaneously. Such an implementation is advantageous in that it provides the capability to measure image stacks without motion of a workpiece or any part of the VFL lens system 300. In various alternative implementations, the optical detector 360 may comprise a sensor with an electronic rolling shutter (ERS) system. For example, a camera system may comprise a black and white CMOS sensor using SXGA resolution coupled with an electronic rolling shutter (ERS) system (e.g., model MT9M001 from Aptina Imaging of San Jose, Calif.).

The VFL lens 370 may be driven by the lens controller 371, which may generate a signal to operate the VFL lens 370. In one embodiment, the lens controller 371 may be a commercial controllable signal generator. In some implementations, the lens controller 371 may be configured or controlled by a user and/or an operating program (e.g., through the lens controller/interface 271, as outlined previously with respect to FIG. 2). In some implementations, the lens controller 371 may control the VFL lens 370 to periodically modulate its optical power (e.g., sinusoidally) and thereby periodically modulate a focus position of the imaging system over a plurality of focus positions along a Z-height direction at a high operating frequency. For example, in some exemplary implementations, a tunable acoustic gradient index of refraction lens may be configured for focal scanning rates as high as 400 kHz, although it should be appreciated that slower focus position adjustments and/or modulation frequencies may be desirable in various implementations and/or applications. For example, in various implementations a periodic modulation of 300 Hz, or 3 kHz, or 70 kHz, or 250 kHz, or the like may be used. In implementations where slower focus position adjustments are used, the VFL lens 370 may comprise a controllable fluid lens, or the like. In various implementations, the periodically modulated VFL lens optical power may define a first periodic modulation phase.

In various implementations, the lens controller 371 may include a drive signal generator portion 372 and a Z-height versus phase calibration portion 373. The drive signal generator portion 372 may operate (e.g., in conjunction with a timing clock 372') to provide a periodic signal. In various implementations, a phase timing signal may be provided by the lens controller 371 that is synchronized with the periodical signal of the drive signal generator portion 372. In various implementations, the periodic signal may have the same operating frequency as the periodically modulated VFL lens optical power, and may have a second periodic modulation phase that has a phase offset relative to the first periodic modulation phase of the periodically modulated VFL lens optical power. In various implementations, the Z-height versus phase calibration portion 373 may provide a first Z-height versus phase characterization that relates respective Z-heights to respective phase timing signal values.

In various implementations, the optical detector 360 (or 360') may be configured to input light from the imaging system including the VFL lens 370, and the focus signal processing portion 377 (or '377) may be configured to determine raw phase timing signal values corresponding to when signal data from the optical detector indicates that an imaged surface region (e.g., of the workpiece 320) is at a focus position. As will be described in more detail below with respect to FIG. 5, the raw phase timing signal values may include a phase offset contribution as related to the phase offset between the first and second periodic modulation phases. As will also be described in more detail below, the phase offset compensating portion 378 may be configured to input raw phase timing signal values corresponding to imaged surface regions and perform a phase offset compensating process that provides Z-height measurements of the imaged surface regions, wherein at least one of Z-height errors or Z-height variations that are related to the phase offset contribution are at least partially eliminated. In various implementations, a phase offset estimation portion 379 of the phase offset compensating portion 378 may determine an estimated value of the phase offset, which may be utilized as part of the phase offset compensating process.

In the example of FIG. 3, the relay lenses 352 and 386 and the VFL lens 370 are designated as being included in a 4f optical configuration, while the relay lens 352 and the tube lens 351 are designated as being included in a Keplerian telescope configuration, and the tube lens 351 and the objective lens 350 are designated as being included in a microscope configuration. All of the illustrated configurations will be understood to be exemplary only, and not limiting with respect to the present disclosure. As part of the Keplerian telescope configuration, a focal distance $F_{TUBE}$ of the tube lens 351 is illustrated as being approximately equidistant to a midpoint between the lenses 351 and 352, as is a focal distance f of the relay lens 352. In alternative implementations, the focal distance $F_{TUBE}$ for the tube lens 351 may be made to be different than the focal distance f of the relay lens 352 (which corresponds to one of the 4 f's of the 4f optical configuration). In various implementations where the tube lens 351 may be included as part of a turret lens assembly, it may be desirable for other tube lenses of the turret lens assembly, when rotated into the operational position, to have a focal point at the same location (i.e., so as to meet the focal point of the relay lens 352).

As described in more detail in the previously incorporated '409 application, the ratio of the focal distance $F_{TUBE}$ to the focal distance f can be utilized to alter the diameter of the collimated beam of workpiece light 355 out of the relay lens 352 relative to the collimated beam of the workpiece light 355 that is input to the tube lens 351. It will be appreciated with respect to the collimated beams of workpiece light 355 that are respectively input to the tube lens 351 and output from the relay lens 352, that in various implementations such collimated beams may be extended into longer path lengths and/or beam splitters may be utilized with respect to such collimated beams for providing additional optical paths (e.g., as directed to different camera systems, etc.)

In various implementations, the illustrated 4f optical configuration permits placing the VFL lens 370 (e.g., which may be a low numerical aperture (NA) device, such as a tunable acoustic gradient index of refraction lens), at the fourier plane of the objective lens 350. This configuration may maintain the telecentricity at the workpiece 320 and may minimize scale change and image distortion (e.g., including providing constant magnification for each Z-height of the workpiece 320 and/or focus position FP). The Keplerian telescope configuration (e.g., including the tube lens 351 and the relay lens 352) may be included between the microscope configuration and the 4f optical configuration, and may be configured to provide a desired size of the projection of the objective lens clear aperture at the location of the VFL lens, so as to minimize image aberrations, etc.

It will be appreciated that in various implementations, certain types of dimensional measurements may require near-diffraction or diffraction-limited imaging. The configuration illustrated in FIG. 3 reduces aberrations by restricting the off-axis extent of the pupil of the objective lens 350 that is imaged into the VFL lens 370. In this configuration, the radial extent may be maintained to be less than the radial extent of the 1st Bessel ring in the refractive index profile of the standing wave of the VFL lens 370 (e.g., a tunable acoustic gradient index of refraction lens) at its lowest resonant frequency $f_{R,MIN}$, as described in more detail in the previously incorporated '409 application. In this manner, light from the microscope configuration (i.e., including the objective lens 350 and the tube lens 351) does not exceed the largest clear aperture $CA_{VFL,MAX}$ of the VFL lens 370. In an implementation where the light did exceed the largest clear aperture, the light could interact with the region of the standing wave of the VFL lens 370 that may have an undesirable refractive index which could increase aberrations and reduce dimensional measurement precision. Some example operations of the VFL lens system 300 will be described in more detail below with respect to FIGS. 4 and 5.

Figure 4:
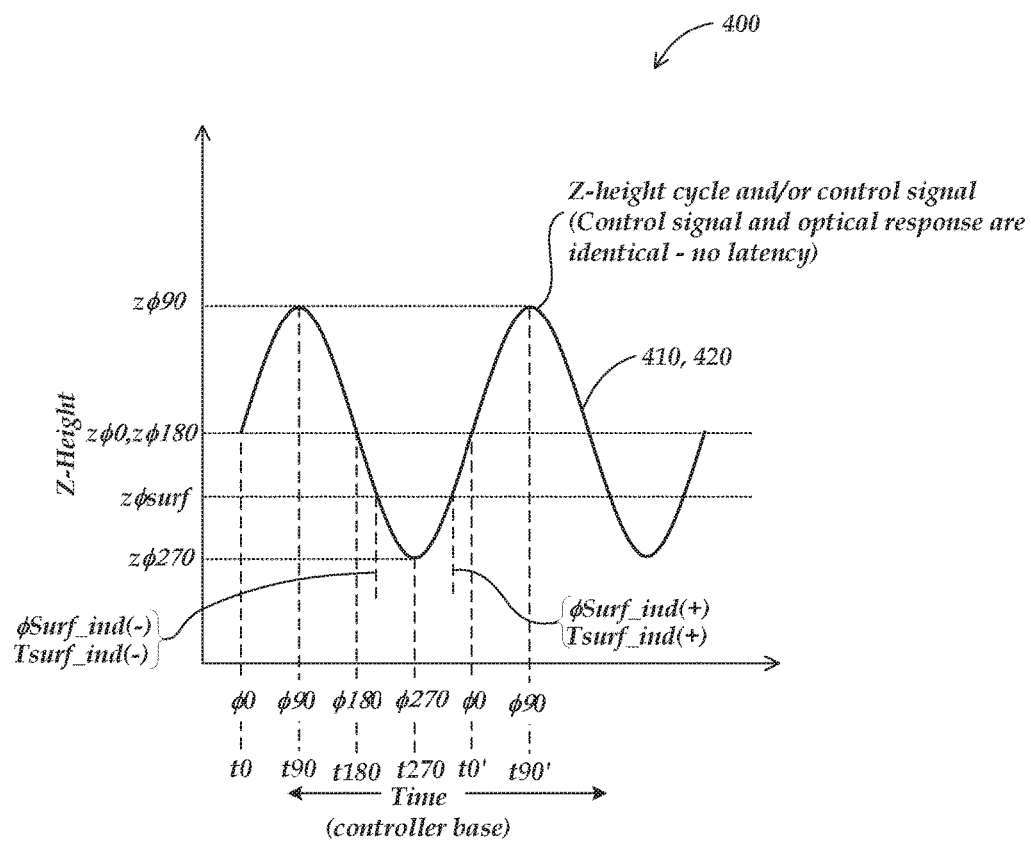
FIG. 4 is a timing diagram illustrating phase timings for a periodically modulated control signal and optical response of the variable focal length lens system of FIG. 3.

FIG. 4 is a timing diagram 400 illustrating phase timings for a periodically modulated control signal 410 and optical response 420 of the VFL lens system of FIG. 3. In the example of FIG. 4, an ideal case is illustrated in which the control signal 410 and the optical response 420 have similar phase timings and are, thus, represented as identical signals (e.g., in contrast to the example of FIG. 5 where the signals are separated by a phase offset, as will be described in more detail below). In various implementations, the control signal 410 may be related to the drive signal that is produced by the drive signal generator 372 of FIG. 3, and the optical response 420 may be representative of the periodically modulated focus position of the imaging system which is controlled by periodically modulating the optical power of the VFL lens 370, as outlined above.

In various implementations, the sinusoidal shapes of the curves 410 and 420 may depend on the lenses in series (e.g., the objective lens 350, VFL lens 370, etc. as illustrated in FIG. 2), for which the optical power of the VFL lens 370 goes through a cycle as indicated in FIG. 4 and is equal to 1/f (where f=focal length). As will be described in more detail below, a Z-height versus phase characterization that relates respective Z-heights to respective phase timing signal values may be established by calibration according to known principles (e.g., in accordance with a mathematical model and/or by repeatedly stepping a surface to a known Z-height, and then manually or computationally determining the phase timing that best focuses an image at the known Z-height, and storing that relationship in a lookup table or the like).

The timing diagram 400 illustrates phase timings (e.g., φ0, φ90, φ180, φ270, etc.) which are equal to respective phase timing signal values (e.g., t0, t90, t180, t270, etc.) of the control signal 410, which correspond to respective Z-heights (e.g., zφ0, zφ90, zφ180, zφ270, etc.) In various implementations, the phase timing signal values (e.g., t0, t90, t180, t270, etc.) may be determined according to a phase timing signal (e.g., as provided by a clock or other technique for establishing a timing relative to the periodic modulation, etc.) It will be understood that the phase timing signal values shown in the timing diagram 400 are intended to be exemplary only and not limiting. More generally, any phase timing signal value will have an associated focus position Z-height within the illustrated range of focus positions (e.g., the range in the illustrated example having a maximum Z-height zφ90 and a minimum Z-height zφ270).

As described above, various techniques (e.g., utilizing points from focus, maximum confocal brightness determinations, etc.) may be used to determine when an imaged surface region is in focus, which may correspond to a Z-height measurement for the imaged surface region. For example, an imaged surface region may be determined to be at a Z-height zφsurf according to when the imaged surface region is in focus. That is, in the illustrated example, at the phase timing φsurf_ind(−), which is equal to the phase timing signal value Tsurf_ind(−), the focus position is at the Z-height zφsurf, and a workpiece surface region located at the Z-height zφsurf will be in focus. Similarly, at the phase timing φsurf_ind(+), which is equal to the phase timing signal value Tsurf_ind(+), the focus position is at the Z-height zφsurf, and the workpiece surface region located at the Z-height zφsurf will be in focus. It will be appreciated that such values may be included in the Z-height versus phase characterization that relates respective Z-heights to respective phase timing signal values, such that when an imaged surface region is determined to be in focus, the corresponding phase timing signal value (e.g., Tsurf_ind(−) may be utilized to look-up the corresponding measured Z-height (e.g., Z-height zφsurf) of the imaged surface region.

In the illustrated example, the phase timing signal values Tsurf_ind(−) and Tsurf_ind(+) correspond to movements of the modulated focus position in respective opposite directions. More specifically, the phase timing signal value Tsurf_ind(−) corresponds to movement of the modulated focus position in a first direction (e.g., downward), while the phase timing signal value Tsurf_ind(+) corresponds to movement of the modulated focus position in a second direction (e.g., upward) that is opposite to the first direction. Due to the control signal 410 and the optical response 420 having similar phase timings in the example of FIG. 4, the phase timing signal values Tsurf_ind(−) and Tsurf_ind(+) of the control signal 410 are shown to correspond to the same Z-height zφsurf. In contrast, as will be described in more detail below with respect to FIG. 5, when the optical response 420 has a phase offset relative to the control signal 410, different Z-heights may be indicated as corresponding to such phase timing signal values, for which a phase offset compensating process may be utilized in accordance with the principles disclosed herein.

Figure 5:
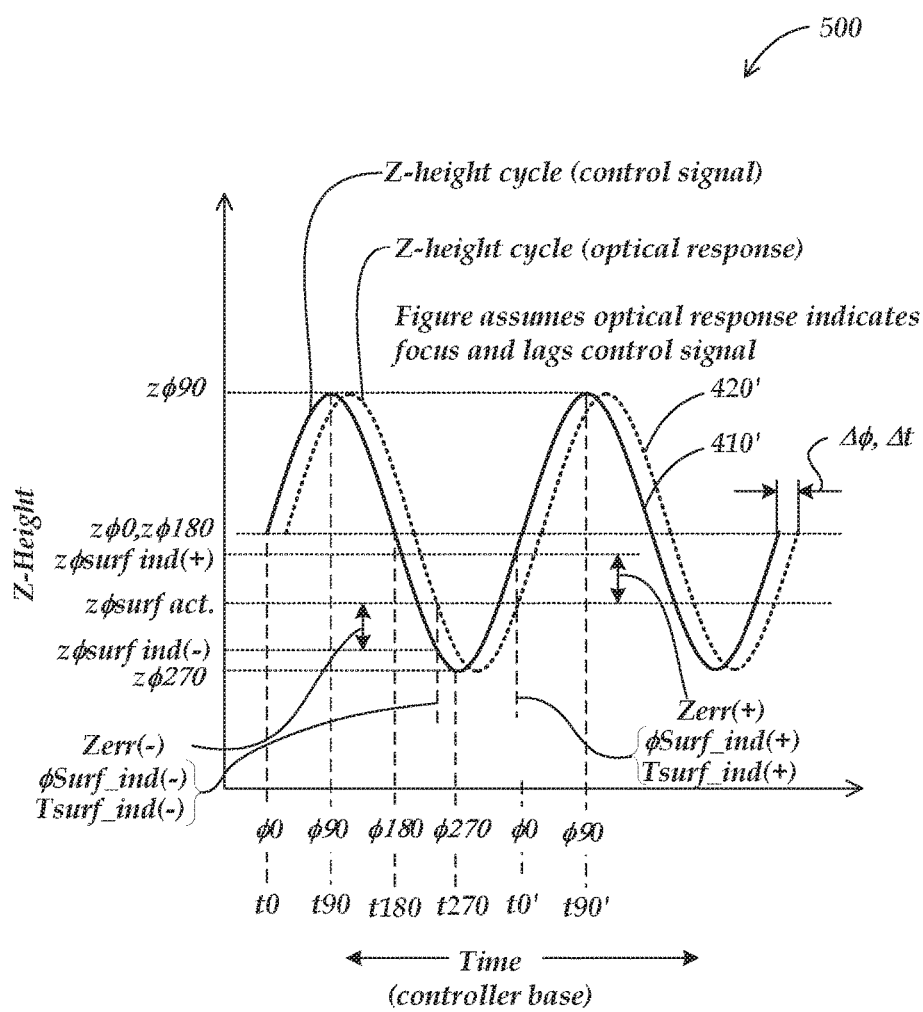
FIG. 5 is a timing diagram illustrating a phase offset between a periodically modulated control signal and an optical response of the variable focal length lens system of FIG. 3.

FIG. 5 is a timing diagram 500 illustrating a phase offset between a periodically modulated control signal 410' and an optical response 420' of the VFL lens system of FIG. 3. As illustrated in FIG. 5, a phase offset contribution corresponds to a delta phase timing $\Delta\varphi$, which corresponds to a delta phase timing signal value $\Delta t$. As a result of the phase offset contribution, when an imaged surface region is actually at a Z-height z$\varphi$surf_act, corresponding phase timing signal values relative to the optical response 420' may indicate other Z-heights relative to the control signal 410'.

That is, in the illustrated example, at the phase timing $\varphi$surf_ind(−), which is equal to the phase timing signal value Tsurf_ind(−) the optical response 420' corresponds to the focus position being at the Z-height z$\varphi$surf_act, however the control signal 410' incorrectly indicates that the focus position is at the Z-height z$\varphi$surf_ind(−). The difference between the Z-height z$\varphi$surf_act and the Z-height z$\varphi$surf_ind(−) is shown to be a Z-height error Zerr(−). Similarly, at the phase timing $\varphi$surf_ind(+), which is equal to the phase timing signal value Tsurf_ind(+), the optical response 420' corresponds to the focus position being at the Z-height z$\varphi$surf_act, however the control signal 410' incorrectly indicates that the focus position is at the Z-height z$\varphi$surf_ind (+). The difference between the Z-height z$\varphi$surf_act and the Z-height z$\varphi$surf_ind(+) is shown to be a Z-height error Zerr(+).

As noted above, the phase timing signal value Tsurf_ind (−) corresponds to movement of the modulated focus position in a first direction (e.g., downward), while the phase timing signal value Tsurf_ind(+) corresponds to movement of the modulated focus position in a second direction (e.g., upward) that is opposite to the first direction. As illustrated, the corresponding Z-height errors Zerr(−) and Zerr(+) may also correspondingly be relatively opposite to one another (e.g., relative to the Z-height z$\varphi$surf_act). In various implementations, the opposite nature of the Z-height errors Zerr (−) and Zerr(+) may be utilized as part of a phase offset compensating process. In accordance with the principles disclosed herein, different phase offset compensating processes may be utilized in various implementations, as will be described in more detail below.

For example, in one configuration a phase offset compensating process may include determining a Z-height measurement of an imaged surface region based on a corresponding set of raw phase timing signal values comprising at least first and second respective subsets of raw phase timing signal values corresponding to movements of the modulated focus position of the imaging system in respective opposite directions. With respect to the example of FIG. 5, a first respective subset of raw phase timing signal values may include at least the phase timing signal value Tsurf_ind(−), and may also include similar phase timing signal values determined during subsequent VFL lens cycles (e.g., within the next VFL lens cycle another phase timing signal value may again be determined when the imaged surface region is again in focus during movement of the modulated focus position in the downward direction, and so on). Similarly, a second respective subset of raw phase timing signal values may include at least the phase timing signal value Tsurf_ind(+), and may also include similar phase timing signal values determined during subsequent VFL lens cycles (e.g., within the next VFL lens cycle another phase timing signal value may again be determined when the imaged surface region is again in focus during movement of the modulated focus position in the upward direction, and so on).

In one implementation, such a phase offset compensating process may more specifically begin with determining a first preliminary Z-height measurement subset (e.g., including at least the Z-height z$\varphi$surf_ind(−)) based on at least one value in the first subset of raw phase timing signal values (e.g., the raw phase timing signal value Tsurf_ind(−)) and the first Z-height versus phase characterization. The process may also include determining a second preliminary Z-height measurement subset (e.g., including at least the Z-height z$\varphi$surf_ind(+)) based on at least one value in the second subset of raw phase timing signal values (e.g., the raw phase timing signal value Tsurf_ind(+)) and the first Z-height versus phase characterization. The process may further include determining a Z-height measurement value (e.g., Z-height z$\varphi$surf_act) that is intermediate between at least one value (e.g., Z-height z$\varphi$surf_ind(−)) in the first preliminary Z-height measurement subset and at least one value (e.g., Z-height z$\varphi$surf_ind(+)) in the second preliminary Z-height measurement subset, and using the determined Z-height measurement (e.g., Z-height z$\varphi$surf_act) as a Z-height measurement value of the imaged surface region. In various implementations, the Z-height measurement value (e.g., Z-height z$\varphi$surf_act) may be determined as the average of at least one value (e.g., Z-height z$\varphi$surf_ind(−)) in the first preliminary Z-height measurement subset and at least one value (e.g., Z-height z$\varphi$surf_ind(+)) in the second preliminary Z-height measurement subset. In various implementations, a controller of the VFL lens system may restrict the operating range of the imaging system to be at less than ⅔ of the maximum operating range and so as to not include peaks or troughs of a periodic signal in the controller (e.g., so as to utilize the above described phase offset compensating process during the relatively linear portions of the sinusoidal curves 410' and/or 420', as opposed to the non-linear portions that occur at the peaks and troughs, etc.)

As another example, in a different configuration a phase offset compensating process may be configured to determine an estimated value of the phase offset and may include a Z-height determination process for determining a Z-height measurement of an imaged surface region based on at least one corresponding raw phase timing signal value and the estimated value of the phase offset. In such a configuration, the Z-height determination process may include determining a compensated phase timing signal value by processing the at least one corresponding raw phase timing signal value with the estimated value of the phase offset to reduce the phase offset contribution, and may further include determining a Z-height measurement based on the compensated phase timing signal value and the first Z-height versus phase characterization. In one implementation, the phase offset compensating portion may include a phase offset estimation portion that is operable to perform an adjustment process that adjusts the estimated value of the phase offset to satisfy a criteria. In one implementation, the criteria is such that when the Z-height determination process is based on the adjusted estimated value of the phase offset and is repeated corresponding to at least first and second respective subsets of raw phase timing signal values corresponding to movements of the modulated focus position of the imaging system in respective opposite directions when imaging a fixed surface region, at least one of a variance or difference between the resulting opposite-direction Z-height measurements is approximately minimized. With respect to the example of FIG. 5, a first respective subset of raw phase timing signal values may include at least the phase timing signal value Tsurf_ind(−) with a resulting Z-height measurement of Z-height z$\varphi$surf_ind(−)), and a second respective subset of raw phase timing signal values may include at least the phase timing signal value Tsurf_ind(+), with a resulting Z-height measurement of Z-height zφsurf_ind(+)). The variance and/or difference between the resulting opposite-direction Z-height measurements in this instance may be equal to the sum of the Z-height errors Zerr(−) and Zerr(+). As will be described in more detail below with respect to FIG. 7, in one implementation the estimated value of the phase offset may be adjusted (e.g., in incremental steps) to determine an estimated value of the phase offset which results in a minimized variance or difference between the resulting opposite-direction Z-height measurements (e.g., so as to achieve a configuration that is more comparable to the example of FIG. 4 where the phase timing signal values Tsurf_ind(−) and Tsurf_ind(+) of the control signal 410' are made to come closer to corresponding to the same Z-height zφsurf_act).

As another example, in another configuration where an estimated value of the phase offset is determined and adjusted, a phase offset compensating process may include imaging a fixed surface region and determining a corresponding set of raw phase timing signal values comprising at least first and second respective subsets of raw phase timing signal values corresponding to movements of the modulated focus position of the imaging system in respective opposite directions. In such a configuration, the first and second respective subsets of raw phase timing signal values may be nominally symmetrically spaced around the 90 degree phase or the 270 degree phase of the first periodic modulation phase, and the estimated value of the phase offset may be adjusted based on the first and second respective subsets of raw phase timing signal values. With respect to the example of FIG. 5, a first respective subset of raw phase timing signal values may include at least the phase timing signal value Tsurf_ind(−), and may also include similar phase timing signal values determined during subsequent VFL lens cycles, and a second respective subset of raw phase timing signal values may include at least the phase timing signal value Tsurf_ind(+), and may also include similar phase timing signal values determined during subsequent VFL lens cycles. Such first and second respective subsets of raw phase timing signal values will be nominally symmetrically spaced around the 270 degree phase of the first periodic modulation phase of the optical response 420', as illustrated in FIG. 5 with respect to the spacing of the raw phase timing signal values Tsurf_ind(−) and Tsurf_ind(+).

In one implementation, the operation of adjusting the estimated value of the phase offset based on the first and second respective subsets of raw phase timing signal values may begin with approximating the first peak phase timing signal value of the 90 degree phase or 270 degree phase of the first periodic modulation phase as an average value of the first and second respective subsets of raw phase timing signal values (e.g., the average value between the raw phase timing signal values Tsurf_ind(−) and Tsurf_ind(+) for the 270 degree phase). The operation may also include establishing a second peak phase timing signal value of the corresponding 90 degree phase or 270 degree phase of the second periodic modulation phase based on the phase timing signal being synchronized with the periodic signal in the controller that has the second periodic modulation phase (e.g., the phase timing signal value t270). The operation may further include adjusting the estimated value of the phase offset to a value corresponding to a difference between the first and second peak phase timing signal values (e.g., so as to achieve a configuration comparable to the example of FIG. 4 where the phase timing signal values Tsurf_ind(−) and Tsurf_ind(+) of the control signal 410' are made to come closer to corresponding to the same Z-height zφsurf_act).

In various implementations, the control signal 410' may be related to various other signals that are produced and/or determined by the VFL lens system. For example, synchronization pulses may be produced by certain electronic circuits or routines of the VFL lens system, and may be synchronized such that they occur at specified phase locations along an optical response and/or drive signal (e.g., as produced by the drive signal generator 372 of FIG. 3). In some instances, documentation may be provided regarding VFL lenses and/or systems that may indicate that provided synchronization pulses are intended to occur at specified locations on a power curve (e.g., the optical response 420'). However, in practice it has been observed that there may be a delay (e.g., a phase delay) between the specified and actual synchronization pulse locations. In addition, it has been observed that this delay tends to vary depending on conditions (e.g., temperature, etc.) In various implementations, the control signal 410' may be a synthetic signal that is representative of, or otherwise synchronized with, the timing of such synchronization pulses, and may correspond to the values of a Z-height versus phase characterization. In one implementation, synchronization pulses may be synchronized with the drive signal that is produced by the drive signal generator 372 of FIG. 3, and may occur at specified phase locations along the drive signal. For example, in various implementations, the optical response 420' may have a phase offset relative to the drive signal, and the control signal 410' (e.g., as representative of the timing of the synchronization pulses) may be synchronized with the drive signal but may also have a phase offset relative to the drive signal. In one implementation, a phase timing signal (e.g., a provided by a clock etc.) may be synchronized with the control signal 410' and/or corresponding synchronization pulses.

Figure 6:
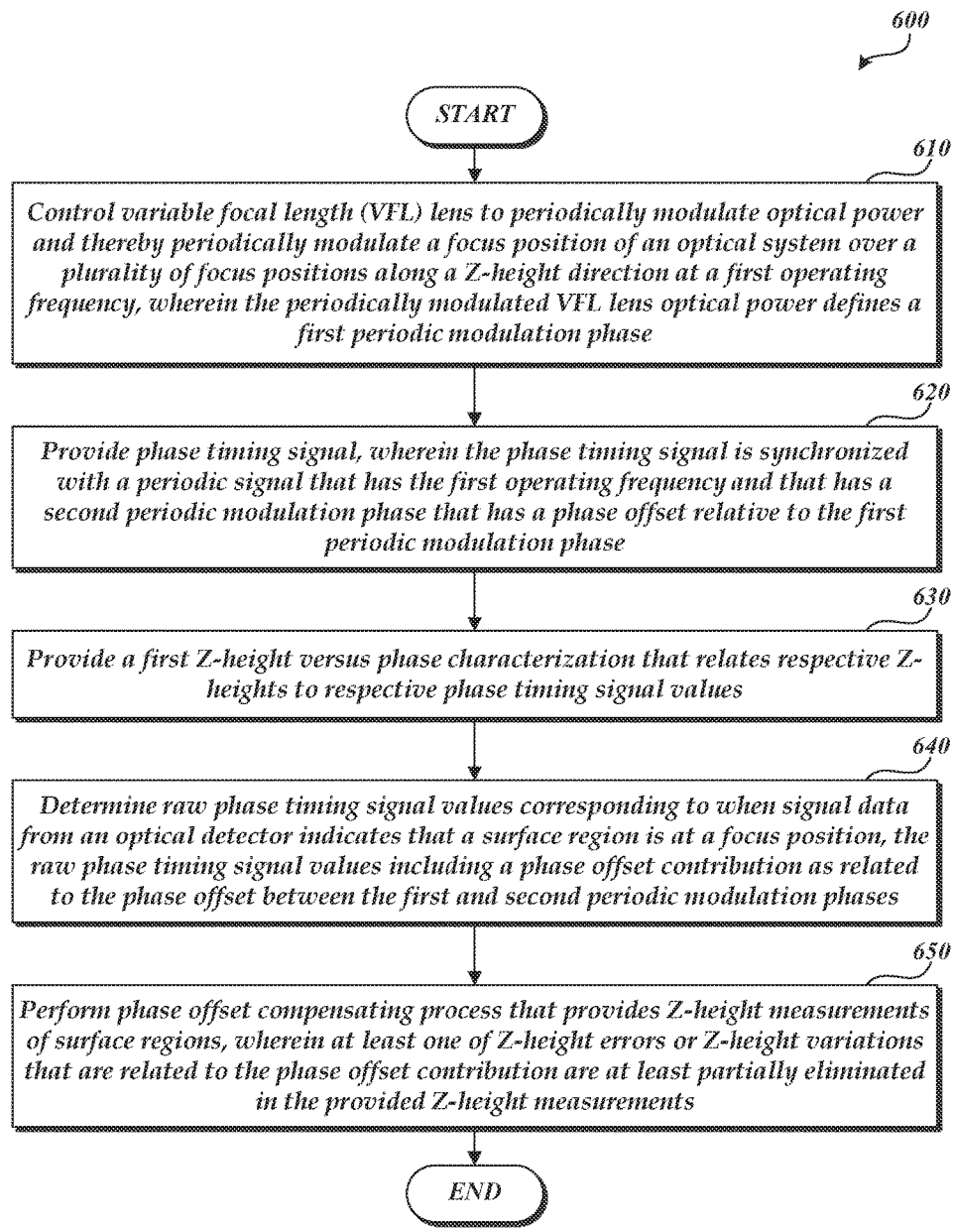
FIG. 6 is a flow diagram illustrating one exemplary implementation of a routine for determining a surface Z-height measurement of a surface region.

FIG. 6 is a flow diagram illustrating one exemplary implementation of a routine 600 for determining a surface Z-height measurement of a surface region. At a block 610, a VFL lens is controlled to periodically modulate its optical power and thereby periodically modulate a focus position of an optical system over a plurality of focus positions along a Z-height direction at a first operating frequency, wherein the periodically modulated VFL lens optical power defines a first periodic modulation phase. At a block 620, a phase timing signal is provided, wherein the phase timing signal is synchronized with a periodic signal that has the first operating frequency and that has a second periodic modulation phase that has a phase offset relative to the first periodic modulation phase.

At a block 630, a first Z-height versus phase characterization is provided that relates respective Z-heights to respective phase timing signal values. At a block 640, raw phase timing signal values are determined corresponding to when signal data from an optical detector indicates that a surface region is at a focus position, the raw phase timing signal values including a phase offset contribution as related to the phase offset between the first and second periodic modulation phases. At a block 650, a phase offset compensating process is performed that provides Z-height measurements of surface regions, wherein at least one of Z-height errors or Z-height variations that are related to the phase offset contribution are at least partially eliminated in the provided Z-height measurements.

Figure 7:
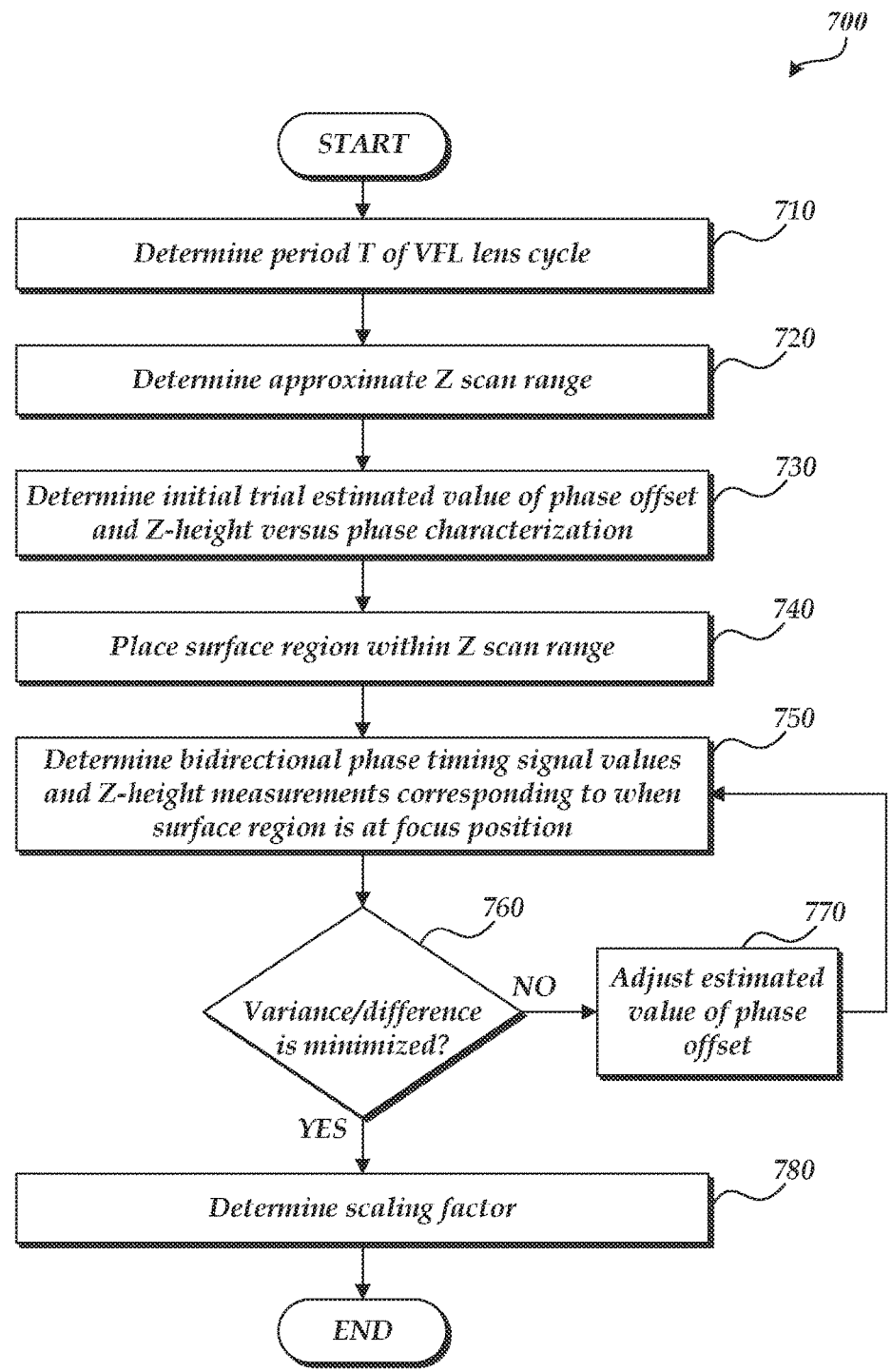
FIG. 7 is a flow diagram illustrating one exemplary implementation of a routine for determining an estimated value of a phase offset.

FIG. 7 is a flow diagram illustrating one exemplary implementation of a routine 700 for determining an estimated value of a phase offset. In the case that the routine 700 is used in a calibration procedure to create or adjust a Z-height versus phase characterization, to be used as outlined herein, the routine 700 may also determine a scaling factor corresponding to the actual Z-scan range of the focus of the VFL lens system.

At a block 710, a period T of the modulation cycle of the VFL lens system is determined. In various implementations, various techniques may be utilized for determining the period T of the periodic modulation cycle. For example, in a configuration where synchronization pulses are generated (e.g., by certain electronic circuits or routines of the VFL lens system, etc.), the period T may be computed as an average period between two synchronization pulses. In an implementation where a high sampling frequency is utilized (e.g., thousands of samples of measured Z-heights per periodic modulation cycle), a median number of samples between two synchronization pulses may be utilized in some instances to determine the period T of the periodic modulation cycle. At a block 720, an approximate Z-scan range of the VFL lens system is determined. In various implementations, the approximate Z-scan range may be based on an optical model of the VFL lens system.

At a block 730, an initial trial estimated value of a phase offset and a Z-height versus phase characterization that relates respective Z-heights to respective phase timing signal values is determined. In various implementations, the Z-height versus phase characterization may be determined based on the period T and the approximate Z-scan range, as well as the initial trial estimated value of the phase offset. In various implementations, the Z-height versus phase characterization may be based on a mathematical or other model (e.g., as including values that correspond to a sine or cosine wave with the specified Z-range, period T, and initial trial estimated value of the phase offset, etc.), or on Z-height-phase characteristics of the system measured experimentally (e.g., a lookup table interpolated using various methods, such as linear approximation, spline interpolation, sine wave fitting, etc.) In various implementations, it may be desirable to make the number of values in the Z-height versus phase characterization approximately equal to the number of samples (e.g., measured Z-heights) that occur between two synchronization pulses, which in some instances may depend on the sampling rate of the VFL lens system. In various implementations, different sampling rates (e.g., thousands of samples per cycle, etc.) may be utilized depending on the desired accuracy of the system.

At a block 740, a surface region (e.g., a mirror in the case of a calibration procedure) is positioned within the VFL lens system Z-scan range. In various implementations, it may be desirable to place the surface region approximately in the middle of the Z-scan range. In implementations where other scan capabilities (e.g., for lateral scans, etc.) are included as part of the VFL lens system, it may be desirable to turn off or otherwise disable such other types of scans in order to reduce the influence of other optical errors on the Z variability of the measured surface location. More specifically, in certain implementations it is desirable to measure repeatedly exactly the same spot on an image surface region of a stationary calibration surface using the Z-height scan capabilities of the VFL lens system.

At a block 750, bidirectional phase timing signal values and corresponding Z-height measurements are determined corresponding to when the stationary imaged surface region is at the focus position. As described above with respect to FIG. 5, in various implementations such operations may include performing a Z-height determination process based on the trial estimated value of the phase offset and repeating operations corresponding to at least first and second respective subsets of raw phase timing signal values corresponding to movements of the modulated focus position of the imaging system in respective opposite directions when imaging a fixed surface region. In various implementations, a number of Z-height measurements may be determined from multiple Z-scans using the current Z-height versus phase characterization. In various implementations, such as where a VFL lens 370 is being operated to scan continuously at a large number of cycles (e.g., thousands, etc.) per second, a Z-height measurement may be quickly determined for each Z-scan (e.g., in both the up and down directions, as described above with respect to FIGS. 4 and 5). In this manner, a large number (e.g., thousands, etc.) of Z-heights may be quickly accumulated (e.g., utilizing a confocal or other system, etc.) when a stationary surface spot on an imaged surface region is being measured.

At a decision block 760, a determination is made as to whether at least one of a trial variance or difference is at least approximately minimized. For example, a standard deviation calculation may be applied to the determined Z-height measurements (e.g., computing their sigma), for determining an overall trial variance or difference. If the overall trial variance or difference has not been sufficiently minimized, the routine proceeds to a block 770, where the trial estimated value of the phase offset is adjusted. For example, the trial estimated value of the phase offset may be adjusted by an incremental (e.g., 0.1 degree phase steps, etc.) or other technique, so as to provide a new trial estimated value of the phase offset. However, this implementation of adjusting the estimated phase offset is exemplary only, and not limiting. For example, in one alternative adjustment method, respective difference or variance values may be determined for a plurality of respective phase offsets over an estimated or predetermined range, which may define a corresponding curve of data points. The minimum of the curve (the minimum variance or difference) may be found by known methods (curve fitting and peak or valley finding, etc.), and the corresponding phase offset value may be used for the estimated phase offset. This may result in an "ideal" and precise adjustment, to an interpolated phase offset value between the initial values used for establishing the curve. These and other alternative methods for performing the operations of block 770 may be apparent to one of ordinary skill in the art based on the various teachings included herein.

If the trial variance or difference is at least approximately minimized, the routine proceeds to a block 780. In various implementations, once the trial variance or difference has been determined to be minimized (e.g., after performing the operations of blocks 750 to 770 as needed to satisfy the requirement(s) of block 760), the corresponding trial estimated value of the phase offset may be utilized as the estimated value of the phase offset for subsequent Z-height measurement operations of the VFL lens system. In various implementations, the estimated value of the phase offset may be utilized as part of one or more processes for individually or collectively determining measured Z-heights, or may be utilized to adjust a previously determined Z-height versus phase characterization to take into account a drift or change in the phase offset. In other words, if an "original" phase offset that corresponds to or underlies a previously determined Z-height versus phase characterization has changed, the difference between it and the new estimated value of the phase offset may be used to shift or adjust the Z-height versus phase characterization to be correct in light of the new estimated value of the phase offset.

At a block 780, in the case that the routine 700 is being used in a calibration procedure to create or adjust a Z-height versus phase characterization, a scaling factor is determined (e.g., for scaling respective Z-height values, etc.) In various implementations, the determination of the scaling factor may include utilization of a calibration object with a known Z-step height, or a single surface may be displaced in Z by a known amount, etc. To determine the scaling factor, the calibration object with the known Z-step height or the surface displaced in Z by a known amount is measured in order to determine corresponding first and second Z-height measurements (e.g., utilizing a Z-height determination process based at least in part on determined first and second corresponding raw phase timing signal values and the estimated value of the phase offset, etc.) A measured Z-height difference is correspondingly determined that corresponds to the difference between the first and second Z-height measurements. A scaling factor is then determined which, when multiplied by or otherwise applied to the measured Z-height difference, results in a value that is equal to the known Z-height difference. In effect, one may understand that this scaling factor can be used to precisely calibrate the range or amplitude of the Z-height focus variations of the VFL lens system. Such a scaling factor can be used to establish the Z-height values used in the Z-height versus phase characterization, or to adjust the Z-height values used in an adjusted Z-height versus phase characterization, if needed or desired.

The problem solutions and related principles disclosed below with reference to FIGS. 8-14 are somewhat different than those disclosed above with reference to FIGS. 1-7. The preceding description of FIGS. 1-7 discloses various combinations of elements, principles and operations that may be used in various implementations of a system that that is operable to provide more accurate Z-height measurements using an imaging system that includes a high speed periodically modulated variable focal length (VFL) lens. In particular, an optical focus detector and a focus signal processing portion indicates when an imaged surface region is at a focus position, with extremely small latency. The related signals and timing information allow a phase offset compensating process to provide Z-height measurements related to an image of a surface region with improved accuracy. In particular, at least one of Z-height errors or Z-height measurement variations present in prior art systems due to phase offset errors arising from electronic and electromechanical latency may be at least partially eliminated. However, while the preceding description enables improved accuracy for a Z-height measurement corresponding to an established image focus position when using a high speed periodically modulated (e.g., 70 kHz) variable focal length (VFL) lens, it does not disclose a complete system for automatically adjusting the image focus position (that is, autofocusing) such that it coincides with a particular workpiece surface, in order to image that particular surface and/or establish its particular Z-height. Generally speaking, the known methods of doing so are slower than desired, and not ideally suited to take advantage of the characteristics of a high speed periodically modulated VFL lens (e.g., a TAG lens).

In various applications, for high throughput it is desirable to perform high speed measurements in either stationary or non-stop moving inspection systems. With respect to well-focused inspection images and Z-height measurements (which are generally based on the "best focus" height determination), the inspection image acquisition rate and the rate at which the Z-height measurements can be performed may be limited by the rate of Z-height focus position adjustment or motion speed. However, innovative variable focus lenses (e.g., TAG lenses) are able to be periodically modulated and change focus at a very high rate (e.g., 70 KHz). Automatically determining and adjusting their image focus position with high very accuracy, at a rate commensurate with their rate of focus variation, has proved problematic. Improved systems and methods for automatically determining and adjusting the image focus position are needed for various high-speed variable focus lenses used for high-speed precision inspection operations.

The following description of FIGS. 8-14 discloses various combinations of elements, principles and operations that may be used in various implementations of a system that that is operable to provide an automatically focused image using an imaging system that includes a high speed periodically modulated VFL lens (e.g., a TAG lens). To briefly review some general operating principles of such imaging systems, it will be appreciated that such imaging systems have a particular focus position (or focus Z height) at a particular timing or phase timing within each period of the modulation. Therefore, a strobe element (e.g., a strobe illumination source, or a fast electronic camera shutter) can be controlled to briefly enable an exposure at a particular phase timing in order to acquire an exposure increment at a desired corresponding focus position. To increase the exposure without blurring the resulting image, the strobe element can be repeatedly strobed at a particular phase timing over a plurality of periods of the periodic modulation that occur during the image exposure (e.g., that occur throughout a camera image integration time). These principles may be understood in greater detail with reference to previously incorporated references, as well with reference to U.S. Pat. Nos. 8,194,307 and 9,143,674, each of which is hereby incorporated herein by reference in its entirety, as well as with reference to copending and commonly assigned U.S. patent application Ser. No. 14/841,051, entitled "Multi-Level Image Focus Using a Tunable Lens in a Machine Vision Inspection System," filed on Aug. 31, 2015, and U.S. patent application Ser. No. 15/360,671, entitled "Machine Vision Inspection System And Method For Obtaining An Image With An Extended Depth Of Field," filed on Nov. 23, 2016, each of which is hereby incorporated herein by reference in its entirety.

According to the principles outlined immediately above, in order to automatically focus an imaging system that includes a high speed periodically modulated VFL lens (e.g., a TAG lens) at a particular surface, a system is required for automatically sensing when a particular phase timing corresponds to focusing at that particular surface, and then operating an exposure strobe time controller to briefly enable an exposure at the sensed particular phase timing. Various implementations of such a system are described below.

Figure 8:
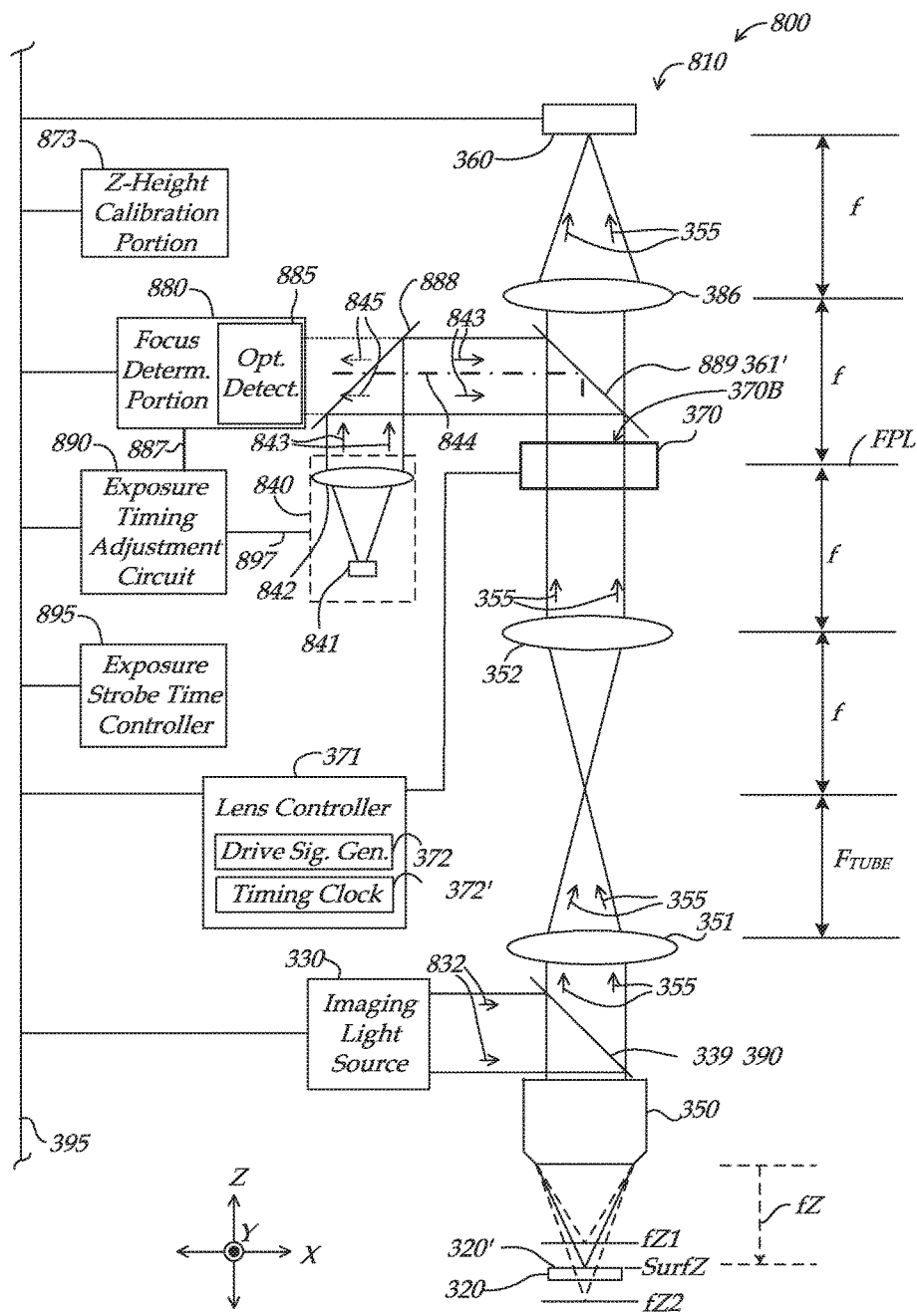
FIG. 8 is a schematic diagram of a first implementation of a variable focal length (VFL) lens system that may be operated to provide an automatically focused image according to principles disclosed herein.

FIG. 8 is a schematic diagram of a first implementation of a system 800 that may be operated to provide an automatically focused image using an imaging system that includes a high speed periodically modulated variable focal length (VFL) lens 370. It will be appreciated that the system 800 of FIG. 8 shares several characteristics with the system 300 of FIG. 3, and may be understood, in large part, by analogy based on previous description. Certain numbered components FIG. 8 may correspond to and/or have similar operations as similarly numbered components of FIG. 3, except as otherwise described below. Therefore, such similar components and shared characteristics will not be described in detail. The following description emphasizes certain elements and aspects of operation of the system 800 that are new or additional in comparison to various system implementations previously described herein. In particular, elements and operations related to automatically adjusting an exposure timing to provide an automatically focused image are emphasized.

The system 800 comprises an imaging system 810, a VFL lens controller 371, a VFL-projected light source 840, a focus determining portion 880, an exposure timing adjustment circuit 890, and an exposure strobe time controller 895. In various implementations, the imaging system 810 includes at least the objective lens 350 (which is configured to input image light arising from a workpiece surface), the VFL lens 370 (which is configured to receive image light transmitted by the objective lens), and the camera 360 (which is configured to receive light transmitted by the VFL lens 370). In the particular configuration shown in FIG. 8, the imaging system 800 also includes the lenses 351, 352, and 386, in a "4f" configuration, previously described with reference to FIG. 3.

The VFL lens controller 371 is configured to control the VFL lens 370 to periodically modulate its optical power and thereby periodically modulate a focus position of the imaging system 810 over a plurality of imaging system focus Z heights along a Z-height direction (e.g., as schematically represented by the coordinate fZ in FIG. 8). Various aspects of the VFL lens controller 371 have been previously described in greater detail herein, and in the incorporated references.

The VFL-projected light source 840 comprises a light source configured to provide VFL-projected light 843 along a focus monitoring light path 844 to a back side 370B of the VFL lens 370 and through the VFL lens 370 and the objective lens 350 to the workpiece surface 320'. In the particular implementation shown in FIG. 8, the VFL-projected light source 840 comprises a light generator 841 (e.g., one or more LED's or laser diodes), and a collimating lens 842. In various implementations the VFL-projected light 843 may be collimated as it is projected along the focus monitoring light path 844 to the backside 370B of the VFL lens 370. In such implementations, the VFL projected light 843 will be focused at the same Z height as the imaging system 810, which may be advantageous for use in the operations and methods outlined below, but is not strictly required in that slight differences in their focus Z height maybe compensated for in electronics or software according to known methods. In various implementations, the light generator 841 may output one or more visible or nonvisible wavelengths, provided that the wavelength(s) are within the sensing range by the optical detector 885.

The focus determining portion 880 comprises an optical detector 885, which is configured to input reflected VFL-projected light 845 that has been reflected from a region of the workpiece surface 320' and back through the objective lens 350 and back through the VFL lens 370 and back along the focus monitoring light path 844. Of course the reflected VFL-projected light 845 also passes through any other optical components situated along this optical path in any particular embodiment. For example, in the particular embodiment shown in FIG. 8, the reflected VFL-projected light 845 is reflected back through objective lens 350, beam splitter 339, lens 351, lens 352, VFL lens 370, and is reflected off of beam splitter 889 and along focus monitoring light path 844, through beam splitter 888, and to optical detector 885.

In response to receiving the reflected VFL-projected light 845 the optical detector 885 outputs at least one optical detector signal that is responsive to a difference between a focus Z height of the VFL-projected light and a Z height of the region on the workpiece surface 320' that reflects it. It will be appreciated that according to the configuration shown in FIG. 8 and outlined above, the VFL-projected light focus Z-height is indicative of the imaging system focus Z-height. The operation of some exemplary optical detectors usable as the optical detector 885 are described in greater detail below. It will be understood that in some implementations the focus determining portion 880 and/or the optical detector 885 may comprise various signal and conditioning and/or processing circuits (not shown), designed according to known principles, to input one or more raw optical detector signals from the optical detector 885 and provide amplification and/or signal processing based on the optical detector signals to output one or more focus deviation signals in a form that is better suited for use by other elements of the system 800.

The exposure timing adjustment circuit 890 inputs the focus deviation signal from the focus determining portion 880 (e.g., on a signal line 887, in some implementations), and determines an exposure timing adjustment signal related to a time when the imaging system focus Z-height approximately coincides with the workpiece surface region Z height, based on the focus deviation signal. Various exemplary implementations usable for the determination of an exposure timing adjustment signal based on a focus deviation signal are described in greater detail below. In various embodiments the exposure timing adjustment circuit 890 may conveniently include a focus determination light control circuit, configured to control the timing of the VFL-projected light 843 during a focus determination time period (e.g., using the control line 897.) In some implementations the VFL-projected light 843 may be provided continuously, and in other implementations strobed, during a focus determination time period. In some implementations the VFL-projected light 843 may be strobed at a time that is adjusted based on the focus deviation signal and/or the exposure timing adjustment signal, as described further below.

In various implementations, the exposure strobe time controller 895 controls an image exposure time of the imaging system 810 (e.g., relative to a phase time of the periodically modulated focus position), wherein the exposure strobe time controller 895 is configured to input the exposure timing adjustment signal from the exposure timing adjustment circuit 890 and provide an adjusted image exposure time based on the exposure timing adjustment signal, wherein the imaging system focus Z-height (e.g., fZ) approximately coincides with the workpiece surface region Z height (e.g., SurfZ) at the adjusted image exposure time. Various exemplary implementations usable for adjusting the image exposure time based on the exposure timing adjustment signal, wherein the imaging system focus Z-height approximately coincides with the workpiece surface region Z height at the adjusted image exposure time, are described in greater detail below.

As previously outlined, the exposure strobe time controller 895 may control an image exposure time by controlling a strobe illumination source, or a fast electronic camera shutter, in various implementations. Digital cameras having an electronic "shutter strobe" function that can create timed sub-exposure increments within an overall image integration period are increasingly available. Such cameras may provide the controlled timings outlined above, using continuous or ambient illumination, in some implementations. However, it is currently more practical to use an illumination source strobe operation. In the implementation shown in FIG. 8, the imaging light source 330 may be operated at the adjusted image exposure time by the exposure strobe controller 895 to output imaging light 832 during an image acquisition. It may be appreciated that in contrast to the VFL-projected light that is used by the focus determination portion 880, illumination from the imaging light source 330 is focused through the objective lens 350 but not through the VFL lens 370 and is therefore not necessarily focused at the workpiece surface 320' at the adjusted image exposure time. This configuration is adequate for some applications, but due to the potentially unknown degree of focus of the image illumination, the resulting image intensity may not be sufficiently robust or predictable enough for the general use of this configuration with a wide variety of workpiece services and/or applications. Configurations where the image illumination is predictably focused on the workpiece surface 320' at the adjusted image exposure time are described below with reference to FIGS. 12 and 13.

A Z-height calibration portion 873 is also shown in FIG. 8. Once an image surface region is acquired based on the adjusted image exposure time, data included in Z height calibration portion 873 may be used to determine a precise Z-height associated with that image, which may be regarded as the Z-height of the surface region in the image. It will be appreciated that the adjusted image exposure time is used in the exposure strobe time controller, and its associated phase timing may therefore be known or determined. In various implementations, the Z-height calibration portion 873 may be substantially similar to the previously described Z height calibration portion 373, which includes data that relates respective Z-heights to respective phases (phase timings) of the periodic focus modulation. In various implementations calibration phase timings in the Z-height calibration portion 873 may be referenced to the periodic focus modulation drive signal available in the lens controller 371, or referenced to a periodic focus modulation sensed and available as a signal in the focus determining portion 880, or referenced to any other signal in the system 800 that is stable and representative of the phase of the periodic focus modulation.

It will be appreciated that in various implementations the various element illustrated in FIG. 8 as connected to the system signal and control bus 395 may exchange signals outlined herein on the bus 395 according to known methods, and/or may exchange signals outlined herein on dedicated interconnections (not shown) according to known methods. Further, it will be appreciated that various elements described with reference to FIG. 8 may be implemented in various appropriate parts of the system 100 shown in FIG. 2, according to known methods and/or by analogy with previous description herein.

Figure 9A:
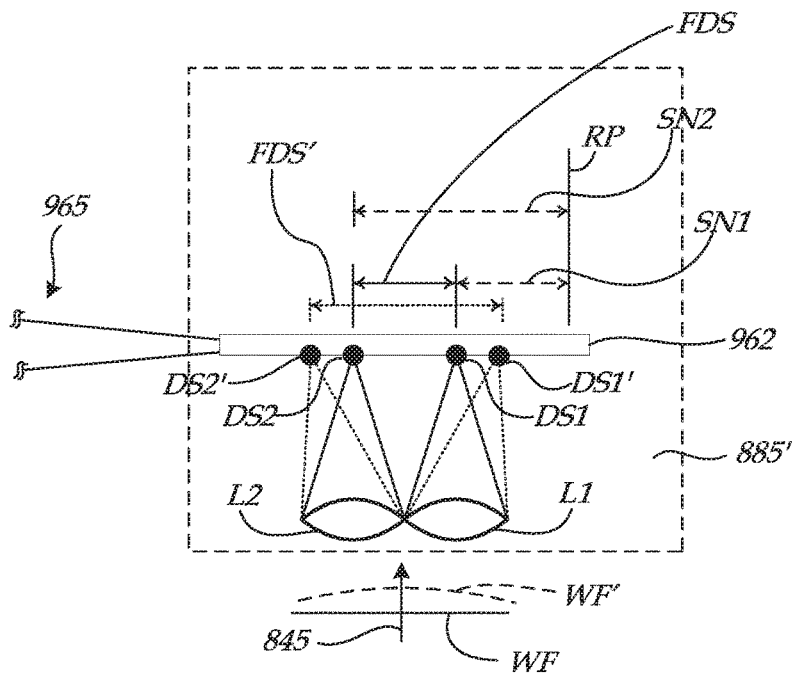
FIGS. 9A and 9B, respectively, show first and second exemplary "directional" type optical detectors usable in the focus determination portion of the VFL lens system of FIG. 8.
Figure 9B:
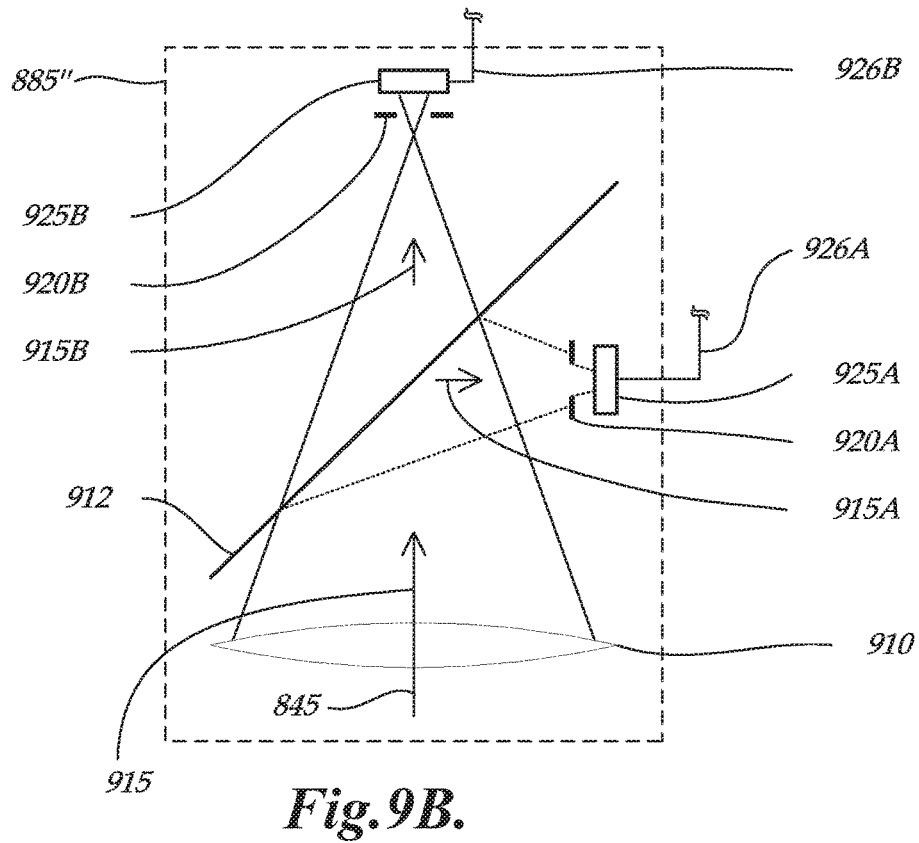

FIGS. 9A and 9B show first and second exemplary "directional" type optical detectors 885' and 885", respectively, usable in various implementations of the focus determination portion 885 of the VFL lens system of FIG. 8.

FIG. 9A shows the optical detector 885' comprising a known type of wavefront curvature detector. In general, a wavefront sensor, as the term is used herein, may be described as sampling at least one local ray angle at a corresponding region along a wavefront of an input light beam to provide at least one corresponding detection signal that depends on the sampled local ray angle. Generally, it is desirable to sample at least two respective local ray angles at two respective corresponding regions that are separated along the wavefront of the input light beam, to provide at least two respective detection signals that depend on the sampled local ray angles. A relationship including the at least two detector signals corresponds to a degree of wavefront curvature of the input focus detection light beam, and the effects of wavefront tilt (as opposed to wavefront curvature) may be detected and rejected as a common mode error that is present in each of the at least two detector signals.

The illustrated optical detector 885' may be characterized as a Shack-Hartmann sensor, and includes lenses L1 and L2 and a photo detector 962 having signal and control line(s) 965. In one embodiment, the lenses L1 and L2 may be micro-lenses. The lenses L1 and L2 each focus input light (e.g., the reflected VFL-projected light outlined above with reference to FIG. 8).

In a "focused" example shown in FIG. 9A, the input light 845 (e.g., the reflected VFL-projected light 845) has a wavefront schematically represented by the wavefront WF. For the wavefront WF, the lenses L1 and L2 produce images that appear as detection spots DS1 and DS2, respectively, on the photo detector 962. In one embodiment, the photo detector 962 may comprise a pair of lateral effect photodiodes (one for each detection spot). In another embodiment, the photo detector 962 may comprise a photodetector array, such as a camera chip, or the like. In any case, the detection spots DS1 and DS2 are at distances SN1 and SN2, respectively, from a reference position RP along the surface of the photo detector 962. The difference between the distances SN1 and SN2 is designated as a distance FDS, which may be regarded as representing a focus deviation signal FDS. The reference position RP from which the distances SN1 and SN2 are measured may be arbitrarily selected. When the photo detector 962 is an array detector, the detection spots DS1 and DS2 may each cover several pixels, in which case a centroid calculation, which may provide sub-pixel position interpolation, may be performed to determine the location of each detection spot.

As is known in the art, the "flat" wavefront WF corresponds to an "in focus" input light, which in this case means that the focus height fZ of the reflected VFL-projected light coincides with the Z height SurfZ of the workpiece surface 320' (see FIG. 8). That is, when the system is properly focused on the workpiece surface (i.e., the reflected VFL-projected light focus height matches the workpiece surface height), the wavefront WF is flat, and the detection spots DS1 and DS2 appear at nominal "null" positions aligned with the optical axes of the corresponding individual lenses, and the focus deviation signal FDS has a nominal or "null" value.

In general, the wavefront WF is not flat when the reflected VFL-projected light focus height deviates from the Z height of the workpiece surface 320'. In an "out of focus" example shown in FIG. 9A, the input light 845 has a wavefront schematically represented by the curved wavefront WF'. For the wavefront WF, the lenses L1 and L2 produce images that appear as detection spots DS1' and DS2', respectively, on the photo detector 962. As is known in the art, the curved wavefront WF' corresponds to an "out of focus" input light, which in this case means that the focus height fZ of the reflected VFL-projected light does not coincide with the Z height SurfZ of the workpiece surface (see FIG. 8). As a result, for the illustrated polarity of wavefront curvature (corresponding to the reflected VFL-projected light focus height being above the workpiece surface 320' in FIG. 8) the detection spots DS1' and DS2' appear at positions that are farther apart than the null positions DS1 and DS2, and the focus deviation signal FDS' is greater than its nominal or "null" value. Conversely, for a wavefront (WF") having a curvature of the opposite polarity (corresponding to the reflected VFL-projected light focus height being below the workpiece surface 320' in FIG. 8) the detection spots (DS1" and DS2") would appear at positions that are closer together apart than the null positions DS1 and DS2, and the focus deviation signal (FDS") would be less than its nominal or "null" value. The optical detector 885' is a "directional" type optical detector because the direction of defocus relative to the workpiece surface 320' can be determined from the polarity of the focus deviation signal.

FIG. 9B shows an optical detector 885" comprising a known type of axial focus location sensor, which is a directional type sensor that may include a lens 910, a beamsplitter 912, a first pinhole aperture 920A and detector 925A, and a second pinhole aperture 920B and detector 925B. In operation the lens 910 inputs the input light 845 (e.g., the reflected VFL-projected light 845) and transmits it as a focused light beam 915 toward the beamsplitter 912, which splits it into first and second measurement beams 915A and 915B. As illustrated in FIG. 9B, the first aperture 920A may be placed at a location that has an optical path length to the lens 910 that is slightly less than the nominal focal length of the lens 910, and the second aperture 920B may be located to have a slightly longer optical path length. Thus, as illustrated in FIG. 9B, when the second measurement beam 915B focuses approximately at the second aperture 920B the second photodetector 925B will receive all of the energy in the second measurement beam 915B and output a second detector signal on a signal line 926B that has a maximum value. At the same time, the focus point of the first measurement beam 915A will be beyond the optical path length to the first aperture 920A. Therefore, the first aperture 920A will occlude a portion of the first measurement beam 915A and the first photodetector 925A will output a first detector signal on a signal line 926A that has a lower value than the second detector signal on the signal line 926B. In general, the difference between the two detector signals will vary in dependence on the axial focus location of the input light 845, which depends on the nominal convergence or divergence of its light rays, which is related to its wave front curvature. The optical detector 885" may therefore respond to the reflected VFL-projected light 845 to when it is focused at the workpiece surface 320' in a manner analogous to the optical detector 885'. The optical detector 885" may be considered a "directional" type optical detector because the direction of defocus relative to the workpiece surface 320' can be determined based on the polarity of a focus deviation signal determined as the difference between its two detector signals, or whether a focus deviation signal determined as a ratio of its two detector signals is greater than or less than one, and so on.

According to another interpretation, the first and second pinhole apertures 920A and 920B may be regarded as confocal apertures related to slightly different focus Z heights. It is the combination of their detector signals that provides a "directional type" focus deviation signal as outlined above. It will be appreciated that if an optical detector includes only one confocal aperture, a varying signal may be obtained which is related to the degree of defocus of the VFL projected light 843 at the workpiece surface 320'. Such an optical detector may be characterized as "magnitude" type optical detector, in that the resulting signal indicates the degree of defocus but not its direction. Although, in some implementations, sequential signal values from a magnitude type optical detector may be processed in relation to other timing information included in the system 800 (e.g., in relation to the phase timing that is known in the drive signal generator 372 of the lens controller 371) in order to determine the direction of defocus as well as its magnitude.

Figure 10:
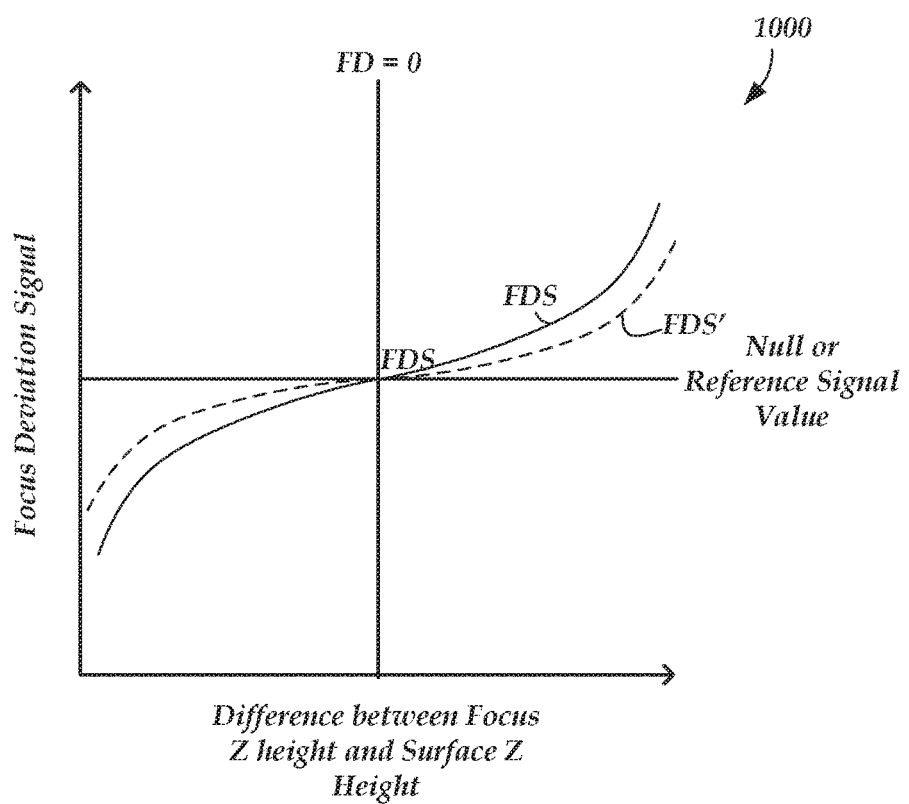
FIG. 10 shows a representative focus deviation signal which may be provided by a focus determination portion including an optical detector such one of those shown in FIG. 9A or 9B.

FIG. 10 is a diagram 1000 showing first and second focus deviation signals FDS and FDS'. As shown in FIG. 10, the focus deviation signals are plotted relative to the difference between the focus Z height of the VFL-projected light and the Z height of the workplace surface 320'. A location where that difference is zero is labeled "FD=0". At that location the first and second focus deviation signals FDS and FDS' are shown to have a null or reference value, which in various implementations is a stable calibrated or known value obtained whenever the focus Z height of the VFL-projected light matches the Z height of the workplace surface 320'. In one example, the focus deviation signal FDS may be regarded as being provided by a directional type focus determination portion including a directional type optical detector such one of those shown in FIG. 9A or 9B, as previously outlined. In some implementations, the signal processing of the raw sensor signals described with relation to FIG. 9A or 9B may permit the focus deviation response curve indicated by the line FDS to be relatively stable regardless of the reflective characteristics of the workpiece surface 320'. In other implementations, the signal processing may be such that the "scaling" or gain of the focus deviation signal FDS varies depending on the reflectivity of the workpiece surface 320'. For example, the focus deviation response curve indicated by the line FDS', may be associated with a workpiece surface 320' having relatively lower reflectivity. However, in either case, both of the focus deviation signals FDS and FDS', are based on optical detector signals that are responsive to a difference between a focus Z height of the VFL-projected light and a Z height of the workpiece surface region, wherein the VFL-projected light focus Z-height is indicative of the imaging system focus Z-height, and therefore both focus deviation signals are indicative of a difference between the imaging system focus Z-height and the Z height of the workpiece surface region.

Figure 11A:
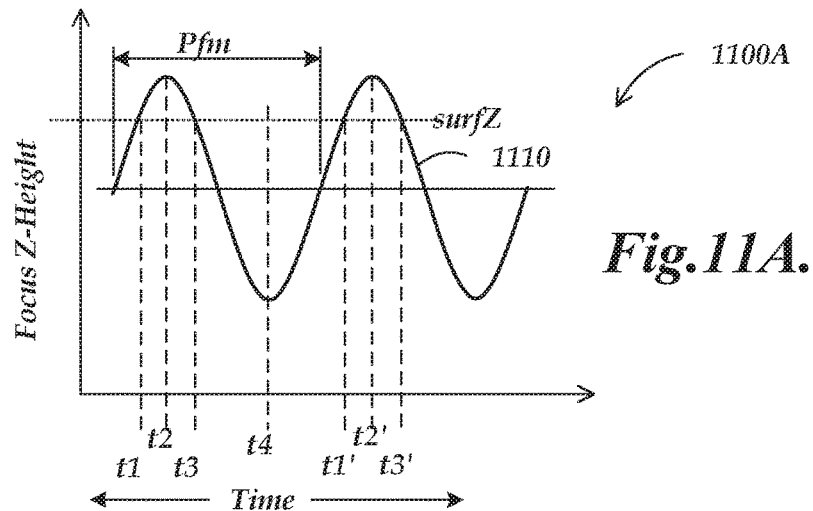
FIG. 11A shows a timing diagram illustrating a relationship between a focus Z height and a surface Z height during a periodic modulation of a focus Z height (e.g., in the VFL lens system shown in FIG. 8).
Figure 11B:
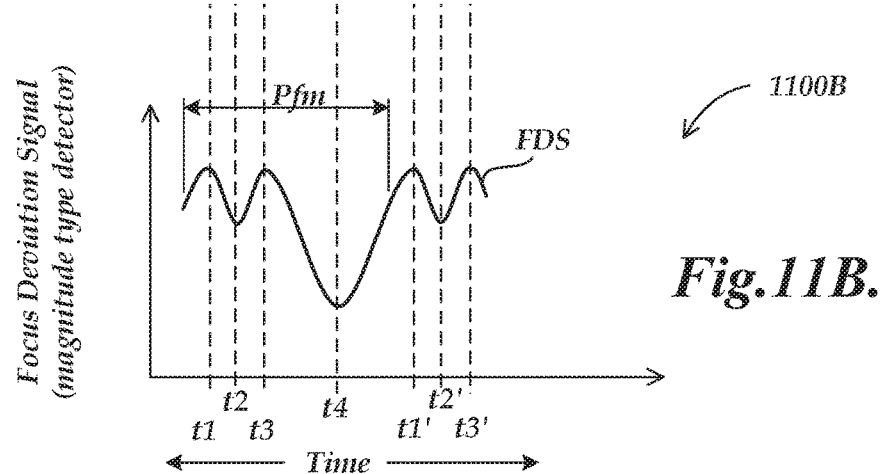
FIG. 11B shows a timing diagram illustrating a representative focus deviation signal corresponding to FIG. 11A, which may be obtained from a "magnitude" type focus determination portion.
Figure 11C:
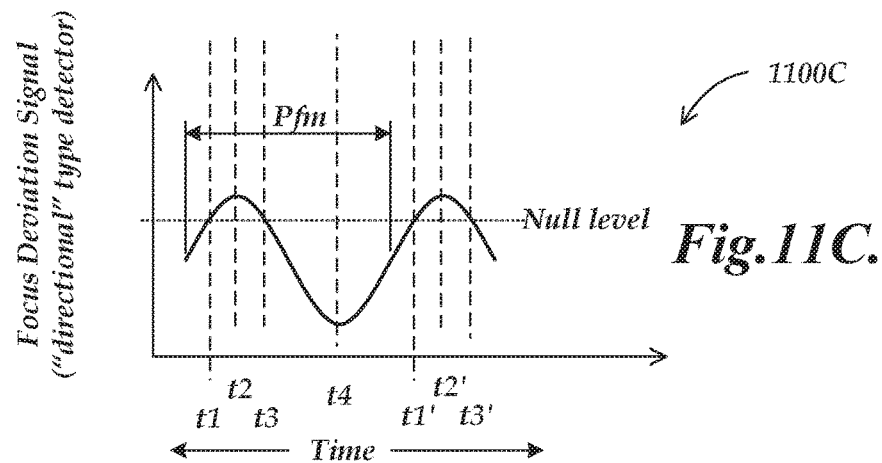
FIG. 11C shows a timing diagram illustrating a representative focus deviation signal corresponding to FIG. 11A, which may be obtained from a "directional" type focus determination portion.

FIGS. 11A through 11C show interrelated timing diagrams to illustrate various aspects of determining an exposure timing adjustment signal related to a time when the imaging system focus Z-height approximately coincides with the workpiece surface region Z height, based on a focus deviation signal. The focus deviation signals shown in FIGS. 11B and 11C are schematic or qualitative representations of the expected focus deviation signal behavior. The scaling of some parts of the signals may be exaggerated related to other parts, for purposes of explanation FIG. 11A shows a timing diagram 1100A illustrating a relationship between a focus Z height 1110 and a workpiece surface Z height surfZ during a periodic modulation of the focus Z height, corresponding to the operation of the periodically modulated VFL lens 370, as previously outline with reference to FIG. 8. The focus modulation period Pfm is shown, which corresponds to the modulation period of the VFL lens 370, as driven by the lens controller 371. In the example shown in FIG. 11A, the focus Z height coincides with the workpiece surface Z height surfZ twice in the focus modulation Pfm, at the times t1 and t3. This pattern repeats for each cycle of the periodic focus modulation, e.g., at the times t1' and t3'. At the time t2 the focus Z height is maximally different than the surface Z height surfZ with a first "polarity", and at the time t4 the focus Z height is maximally different than the surface Z height surfZ with the opposite polarity.

FIG. 11B shows a timing diagram 1100B illustrating a representative focus deviation signal FDS corresponding to the conditions illustrated in FIG. 11A. The focus deviation signal FDS may be obtained from a "magnitude" type focus determination portion (e.g., a focus determination portion including a single confocal optical detector, as previously outlined in discussion related to FIG. 9B) operated as previously outlined with reference the focus determination portion 880 shown in FIG. 8. In one implementation, the illustrated continuous focus deviation signal FDS may be provided by a low latency optical detector 885 operating in a cooperation with continuous illumination from the VFL-projected light source 840, at least during a focus determination time period, as described in greater detail below. In the example shown in FIG. 11B, when the focus Z height coincides with the surface Z height surfZ at the times t1 and t3 (see FIG. 11A), the focus deviation signal FDS has a maximum or peak value. This pattern repeats for each cycle of the periodic focus modulation, e.g., at the times t1' and t3'. At the time t2 the focus Z height is maximally different than the surface Z height surfZ with a first "polarity", and at the time t4 the focus Z height is maximally different than the surface Z height surfZ with the opposite polarity (see FIG. 11A), resulting in the respective trough or "negative peak" minimums shown for the focus deviation signal FDS shown at the times t2 and t4.

As previously outlined with reference to FIG. 8, the focus deviation signal FDS shown in FIG. 11B may be output from the focus determination portion 880 to the exposure timing adjustment circuit 890. The exposure timing adjustment circuit 890 inputs the focus deviation signal FDS and determines an exposure timing adjustment signal related to a time when the imaging system focus Z-height approximately coincides with the workpiece surface region Z height, based on the focus deviation signal FDS. In one implementation, exposure timing adjustment circuit 890 may comprise a low latency peak detection circuit configured to output or initiate a pulse or trigger signal by detecting the peak of the focus deviation signal FDS at the time t1 or t3, or both. In this example, such pulses or trigger signals may be regarded as exposure timing adjustment signals. Various types of suitable low latency peak detector circuits may be configured according to know principles. For example, some implementations may include the use of commercially available peak detection IC's, which may be configured according to application notes available from their manufacturers to provide various functions including outputting a trigger signal as outlined above in response to a peak detections, and/or resetting after a predetermined time period or input signal change, or the like.

As previously outlined with reference to FIG. 8, the exposure strobe time controller 895 is configured input exposure timing adjustment signals from the exposure timing adjustment circuit 890 and provide an adjusted image exposure time based on the exposure timing adjustment signal, wherein the imaging system focus Z-height approximately coincides with the workpiece surface region Z height at the adjusted image exposure time. In various exemplary implementations consistent with the above description, the exposure strobe time controller 895 may briefly enable or activate a strobe element, as triggered by the timing of the exposure timing adjustment signal or trigger signal outlined above, to effectively control a brief image exposure at the particular phase timing corresponding to the trigger signal. To increase the exposure without blurring the resulting image, during an image acquisition time period comprising a camera image integration period spanning a plurality of the focus modulation periods, the exposure strobe time controller 895 may be configured to repeat the brief image exposure as outlined above during each of the focus modulation periods, to provide an overall image exposure at a desired level. In one such implementation, the exposure strobe time controller 895 may be configured to be repeatedly triggered by the exposure time adjustment signal outlined above. In another such implementation, the exposure strobe time controller 895 may include a timing clock that is synchronized with the periodic focus modulation (e.g., in relation to the periodic drive signal that is known in the drive signal generator 372 of the lens controller 371). In such a case it may be configured to register the phase timing of the exposure time adjustment signal "trigger signal" outlined above (e.g., the phase timing of t1, or t3, or both), and repeat the brief image exposure at the same phase timing(s) during each of the focus modulation periods throughout the image acquisition time period, based on its timing clock and the registered phase timing.

As previously outlined, in some embodiments the strobe element controlled by the exposure strobe time controller 895 may be a fast electronic camera shutter. In other embodiments the strobe element controlled by the exposure strobe time controller 895 may be a strobed imaging light source (e.g., the imaging light source 330 shown in FIG. 8). A controllable light source driver (power source) may be included in the exposure strobe time controller 895 or the light source, and may be controlled by, or based on, the exposure time adjustment signal "trigger signal".

FIG. 11C shows a timing diagram 1100C illustrating a representative focus deviation signal FDS corresponding to the conditions illustrated in FIG. 11A. The focus deviation signal FDS may be obtained from a "directional" type focus determination portion (e.g., a focus determination portion including one of the optical detectors 885' or 885" shown in FIG. 9A or 9B, respectively, which operates to provide the focus deviation response curve described with reference to FIG. 10). In one implementation, the illustrated continuous focus deviation signal FDS shown in FIG. 11C may be provided by a low latency optical detector 885 (e.g., the optical detector 885", using low latency photodetectors) operating in a cooperation with continuous or varied phase timing strobed illumination from the VFL-projected light source 840, at least during a focus determination time period. In the example shown in FIG. 11C, when the focus Z height coincides with the surface Z height surfZ at the times t1 and t3 (see FIG. 11A), the focus deviation signal FDS has the null level output value (as previously outlined with reference to FIG. 10.) This pattern repeats for each cycle of the periodic focus modulation, e.g., at the times t1' and t3'. At time t2 the focus Z height is maximally different than the surface Z height surfZ with a first "polarity", and at time t4 the focus Z height is maximally different than the surface Z height surfZ with the opposite polarity (see FIG. 11A), resulting in the respective positive and negative signal peaks shown for the focus deviation signal FDS shown at the times t2 and t4.

As previously outlined with reference to FIG. 8, the focus deviation signal FDS shown in FIG. 11C may be output from the focus determination portion 880 to the exposure timing adjustment circuit 890. The exposure timing adjustment circuit 890 inputs the focus deviation signal FDS and determines an exposure timing adjustment signal related to a time when the imaging system focus Z-height approximately coincides with the workpiece surface region Z height, based on the focus deviation signal FDS. In one implementation exposure timing adjustment circuit 890 may comprise a low latency comparator circuit configured to use the "Null" signal level as a reference level and output or initiate a pulse or trigger signal when the focus deviation signal FDS matches the reference level (e.g., at the time t1 or t3, or both). In this example, such pulses or trigger signals may be regarded as exposure timing adjustment signals.

The use of such pulses or trigger signals in an exposure strobe time controller (e.g., the exposure strobe time controller 895) has been previously described with reference to FIG. 11B, and may follow similar principles in this implementation.

Figure 12:
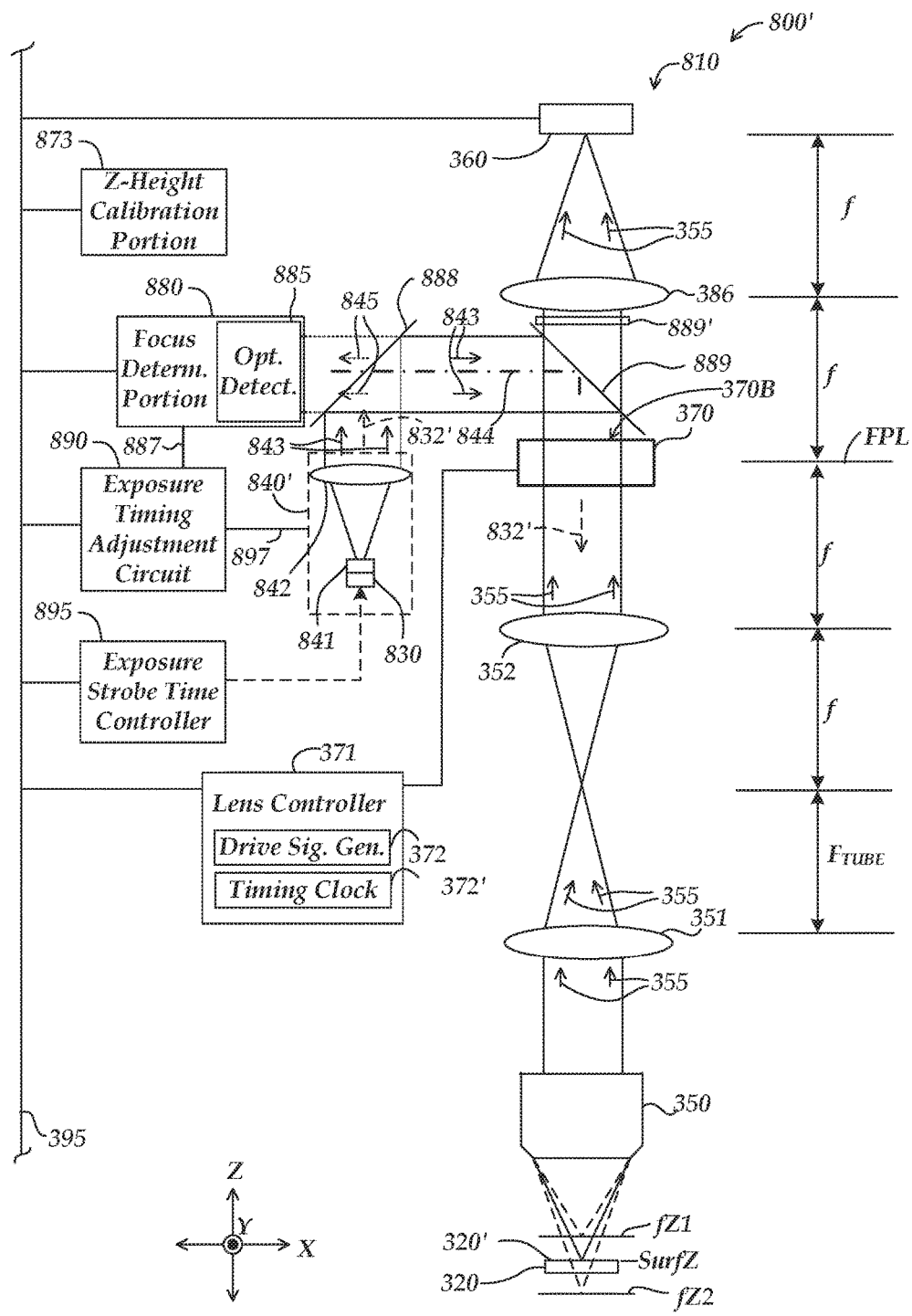
FIG. 12 is a schematic diagram of a second implementation of a VFL lens system that may be operated to provide an automatically focused image according to principles disclosed herein.
Figure 13:
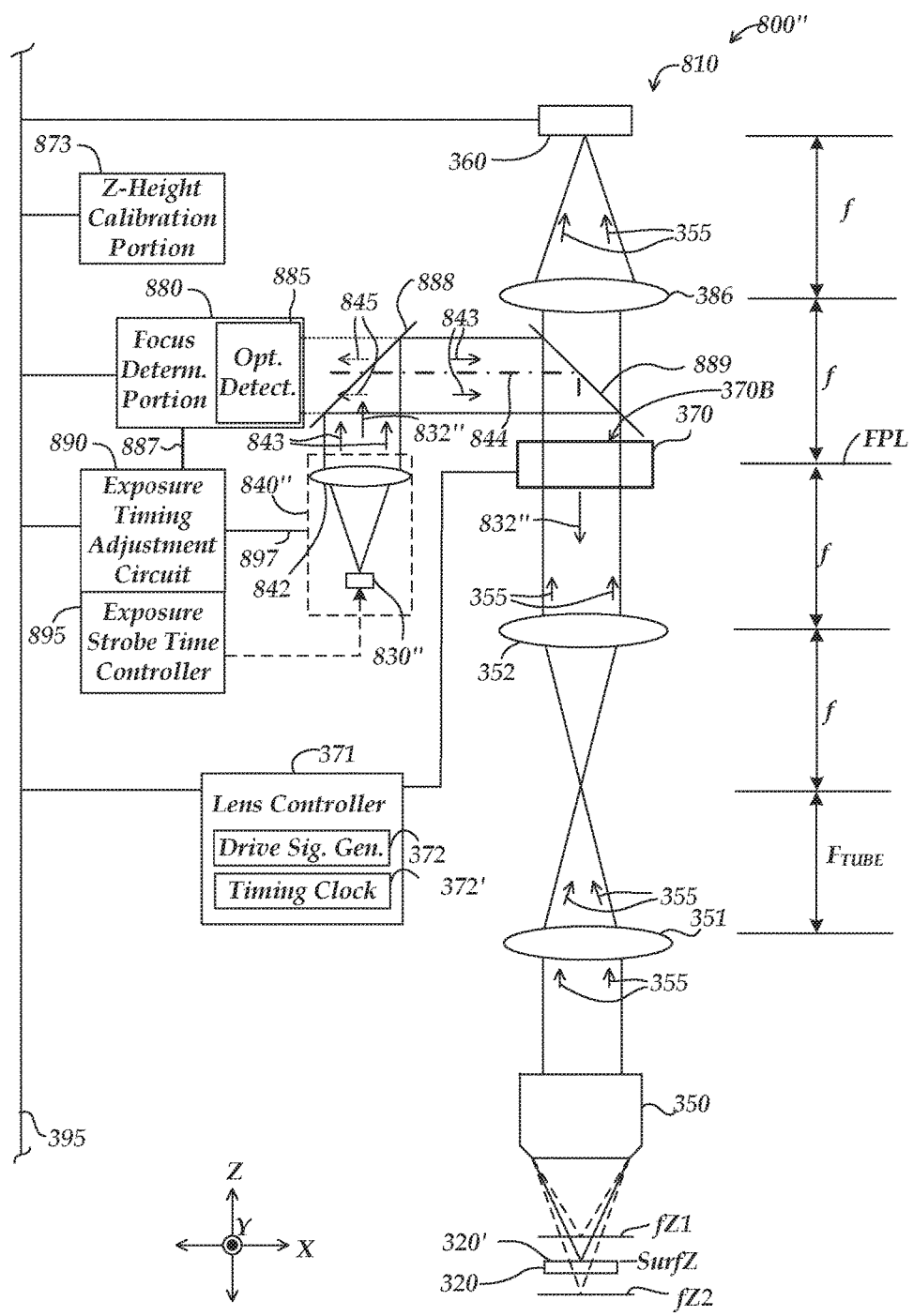
FIG. 13 is a schematic diagram of a third implementation of a VFL lens system that may be operated to provide an automatically focused image according to principles disclosed herein.

FIG. 12 and FIG. 13 are schematic diagrams of second and third implementations of a system that may be operated to provide an automatically focused image using an imaging system that includes a high speed periodically modulated VFL lens. It will be appreciated that the systems of FIGS. 12 and 13 share several characteristics with the system 800 or FIG. 8, and may be understood, in large part, by analogy based on previous description. Certain numbered components FIGS. 12 and 13 may correspond to and/or have similar operations as similarly numbered components of FIG. 8, except as otherwise described below. Therefore, such similar components and shared characteristics will not be described in detail. The following description emphasizes certain elements and aspects of operation that are new or additional in comparison to the system implementation(s) previously described with reference to FIG. 8. In particular, elements and operations related to different implementations for providing and controlling the light used for image acquisition, in relation to providing and controlling the VFL-projected light 843 used for focus determination, are emphasized.

FIG. 12 is a schematic diagram of a second implementation of a system 800' that may be operated to provide an automatically focused image using an imaging system that includes a high speed periodically modulated variable focal length (VFL) lens 370. The system 800' comprises an imaging system 810, a VFL lens controller 371, a light source 840', a focus determining portion 880, an exposure timing adjustment circuit 890, and an exposure strobe time controller 895, which may be configured and operated according to previously outlined principles, except as otherwise described below.

In contrast to the light source 840 described with reference to FIG. 8, which is solely a VFL-projected light source that provides the VFL-projected light 843, a combined light source 840' is shown in FIG. 12. The combined light source 840' is configured to provide both the VFL-projected light 843, and imaging light 832', originating from respective light generators 841 and 830, respectively. In various implementations the light generators 841 and 830 may output different visible or nonvisible wavelengths, provided that the wavelength(s) in the VFL projected light 843 are within the sensing range by the optical detector 885, and the wavelength(s) in the imaging light 832' are within the sensing range of the camera 360.

It will be understood that, in contrast to the configuration shown in FIG. 8, in the implementation described here the imaging light 832' that is used for image acquisition is VFL-projected image light that is always focused at workpiece surface 320' at the adjusted image exposure time, which is desirable in a number of applications.

The light generator 830 in the combined light source 840' may be controlled by the exposure time controller 895 to expose an image at the adjusted image exposure time, during an image acquisition time period, according to previously outlined principles. In various embodiments, the light generator 841 in the combined light source 840' may be independently controlled by a focus determination light control circuit (e.g., included in the exposure timing adjustment circuit 890), configured to control the timing of the VFL-projected light 843 during a focus determination time period (e.g., using the control line 897.) In some implementations the VFL-projected light 843 may be provided continuously, and in other implementations strobed, during a focus determination time period. In some implementations the VFL-projected light 843 may be strobed at a time that is adjusted based on the focus deviation signal and/or the exposure timing adjustment signal (e.g., as described further below with reference to FIG. 14.) In some implementations, the image acquisition time period may overlap with the focus determination time period. In such implementations, a suitable narrowband wavelength filter 889' may be included along the imaging optical path between the beam splitter 889 and the camera 360 to prevent the wavelengths in the reflected VFL-projected light 845 from affecting the acquired image. Of course if the image acquisition time period does not overlap with the focus determination time period, the wavelength filter 889' is not required.

FIG. 13 is a schematic diagram of a third implementation of a system 800" that may be operated to provide an automatically focused image using an imaging system that includes a high speed periodically modulated variable focal length (VFL) lens 370. The system 800" comprises an imaging system 810, a VFL lens controller 371, a light source 840", a focus determining portion 880, an exposure timing adjustment circuit 890, and an exposure strobe time controller 895, which may be configured and operated according to previously outlined principles, except as otherwise described below.

In contrast to the light source 840' described with reference to FIG. 12, single-generator light source 840" is shown in FIG. 12. The system 800 is configured to use the single-generator light source 840" to provide both the VFL-projected light 843, and the imaging light 832, originating from same generator 830". In various implementations the light generator 830" in the single-generator light source 840" may output visible or nonvisible wavelength(s) that are within the sensing range by the optical detector 885 and the camera 360. It will be understood that, similar to the configuration shown in FIG. 12, in the implementation described here the imaging light 832 that is used for image acquisition is a VFL-projected image light that is always focused at workpiece surface 320' at the adjusted image exposure time.

In this implementation, the exposure timing adjustment circuit 890 and exposure time controller 895 may be merged and/or indistinguishable from share control of the single generator 830" (e.g., using the signal line 897). The light generator 830" may be controlled to expose an image at the adjusted image exposure time during an image acquisition time period, and controlled by a focus determination light control circuit in the exposure timing adjustment circuit 890 during a focus determination time period.

In some implementations, these operations may be performed during independent focus determination and image acquisition time periods, according to previously described principles. However in other implementations, because the imaging light 832, the VFL-projected light 843, and the reflected VFL projected light 845 are all "the same light" provided by the same light source 840", the focus determination and image acquisition periods may overlap, at least during some periods of operation. For example, it will be appreciated that during an "in focus" image acquisition according to previously outlined principles, the focus determination portion 880 and the exposure timing adjustment circuit 890 can continue to operate as outlined above by inputting a portion of the strobed VFL-projected light that is used for imaging (that is, the "split" portion that is returned to the beam splitter 889 and reflected along the focus monitoring light path 844). The previously described focusing principles are compatible with the use of either continuous or strobed light in the focus determination portion 880, and/or the associated circuits and/or routines may be readily adaptable to the use of strobed light by one of ordinary skill in the art, based on the principles disclosed herein. As such, it will be appreciated that once the imaging system focus position has been arranged to coincide with the workpiece surface 320' according to previously outlined principles, the system 800" may be operated as a "tracking autofocus" system that may continuously focus on, and image, a variable height workpiece surface 320' as it is scanned across the field of view of the imaging system 810. It will be further appreciated that when the focus deviation signal provided by focus determination portion 880 indicates that a workpiece surface 320' is out of focus, image acquisition operations may be interrupted. Light source 840" may be operated in a continuous or strobed mode to support automatic focusing operations according to principles described previously herein, until the imaging system 810 is once again focused at the workpiece surface 320'.

Figure 14:
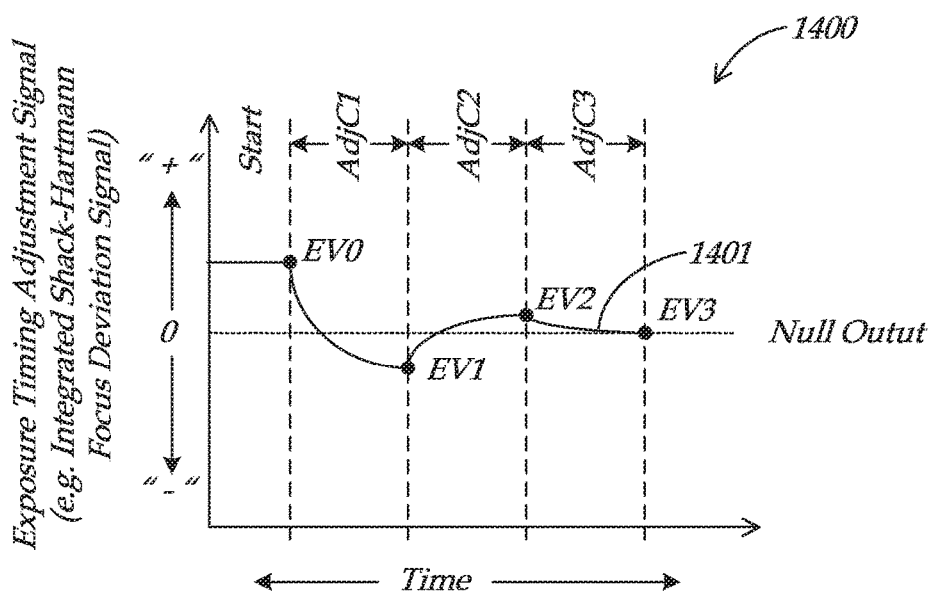
FIG. 14 shows a timing diagram illustrating certain aspects of determining an exposure timing adjustment signal in one implementation of a "magnitude" type focus determination portion.

FIG. 14 shows a timing diagram 1400 illustrating certain aspects of determining an exposure timing adjustment signal using one implementation of a "magnitude" type focus determination portion, in combination with a relatively slow optical detector. In some implementations, the use of low latency optical detectors and/or low latency circuits (e.g., latencies on the order of microseconds, or one microsecond, or less) as previously outlined herein may be impractical. However, if strobed illumination is input to the focus determination portion 880, slower detectors and circuits may be allowed during a focus determination. For example, the timing diagram 1400 shows an integrated focus deviation signal 1401 may be used as, and/or determine, an exposure timing adjustment signal.

In the example shown in FIG. 14, during a "Start" time period the reflected VFL projected light (e.g., the previously described light 845) is strobed at a consistent phase timing, throughout a plurality of periods of the periodic focus modulation, and a signal integrator in the focus determination portion 880 accumulates the integrated focus deviation signal.

In some implementations, the signal integrator may simply comprise a "slow" photo detector in the optical detector 885 which accumulates the photons the various strobe pulses. For example, if the VFL lens 370 is periodically modulated at a frequency of 70 kHz, the modulation period is approximately 14 μs. A slow photo detector may have a response time on the order of 150 μs (or more), during which at least 10 strobe pulses at a particular phase timing may be accumulated and "integrated" by such a photo detector. In any case, the length of the "adjustment cycle" time periods illustrated in FIG. 14, may be selected by one of ordinary skill in the art based on the response time of the signal integrator to provide desirable operating characteristics.

With reference to the exemplary focus deviation signal shown in FIG. 11C, it may be said that based on the positive ending value EV0 of the integrated focus deviation signal at the end of the "Start" time period, the particular phase timing of the strobed pulses throughout the "Start" time period falls somewhere in the range between t1 and t3. In various implementations, the exposure timing adjustment circuit 890 may be configured to perform a "phase timing search" to identify a phase timing which produces a null output for the integrated focus deviation signal, which corresponds to focusing on the workpiece surface 320' according to previously described principles.

For example, in one implementation the exposure timing adjustment circuit 890 may simply adjust the phase timing by advancing the phase timing a preset amount of 60 degrees during the first adjustment cycle time period AdjC1 and evaluate the difference between the ending value EV1 and the Null output level and/or the previous ending value EV0, in order to determine a next adjustment amount. In the example shown in FIG. 14, because the ending value EV1 is less than the null output level (in contrast to EV0), and closer to the null output level than EV0, the exposure timing adjustment circuit 890 may adjust the phase timing by delaying the phase timing by an amount less than 60 degrees, for example 30 degrees. Operation may continue in an analogous manner to determine the ending values EV2 and EV3, after further adjustments. When an ending value is sufficiently close to the Null output level (e.g., EV4), the corresponding particular phase timing used during the last adjustment cycle time period (e.g., during AdjC3) may be taken as a phase timing corresponding to a focus condition. This phase timing value may be considered an exposure timing adjustment signal derived from the focus deviation signal, and output to the exposure strobe time controller 895, which may use this phase timing directly as the adjusted image exposure time, according to previously outlined principles.

It will be appreciated that once the imaging system focus position has been arranged to coincide with the workpiece surface 320' according to previously outlined principles, a "tracking autofocus" system may be providing using the principles outlined above with reference to FIG. 14. For example, in some implementations, image acquisition may be suspended periodically (e.g., every 14 milliseconds, or 1000 periods of the periodic modulation, or less). Because only minimal focus adjustments may be needed in order to continuously focus on a scanned surface, the process outlined for FIG. 14 may take on the order of 10 millisecond or less, despite the use of relative slow photo detectors and/or circuits in various embodiments.

While preferred implementations of the present disclosure have been illustrated and described, numerous variations in the illustrated and described arrangements of features and sequences of operations will be apparent to one skilled in the art based on this disclosure. Various alternative forms and combinations of disclosed elements and/or operations may be used to implement the principles disclosed herein. The various implementations described above can be combined to provide further implementations. All of the U.S. patents and U.S. patent applications referred to in this specification are incorporated herein by reference, in their entirety. Aspects of the implementations can be modified, if necessary to employ concepts of the various patents and applications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled.

What is claimed is:

1. A system for providing an automatically focused image using an imaging system that includes a high speed periodically modulated variable focal length (VFL) lens, the system comprising:
   an imaging system including at least an objective lens configured to input image light arising from a workpiece surface, a VFL lens configured to receive image light transmitted by the objective lens, and a camera configured to receive light transmitted by the VFL lens;
   a VFL lens controller configured to control the VFL lens to periodically modulate its optical power and thereby periodically modulate a focus position of the imaging system over a plurality of imaging system focus Z heights along a Z-height direction,
   a VFL-projected light source, comprising a light source configured to provide VFL-projected light along a focus monitoring light path to a back side of the VFL lens and through the VFL lens and the objective lens to the workpiece surface;
   a focus determining portion comprising an optical detector configured to input reflected VFL-projected light that has been reflected from a workpiece surface region and back through the objective lens and back through the VFL lens and back along the focus monitoring light path, and to provide at least one optical detector signal that is responsive to a difference between a focus Z height of the VFL-projected light and a Z height of the workpiece surface region, wherein the VFL-projected light focus Z-height is indicative of the imaging system focus Z-height, and the focus determining portion outputs at least one focus deviation signal based on the at least one optical detector signal;
   an exposure timing adjustment circuit, which inputs the focus deviation signal and determines an exposure timing adjustment signal related to a time when the imaging system focus Z-height approximately coincides with the workpiece surface region Z height, based on the focus deviation signal; and
   an exposure strobe time controller which controls an image exposure time of the imaging system, wherein the exposure strobe time controller is configured to input the exposure timing adjustment signal and automatically provide an adjusted image exposure time based on the exposure timing adjustment signal, wherein the imaging system focus Z-height approximately coincides with the workpiece surface region Z height at the adjusted image exposure time, and
   the system is configured to provide a focused image comprising at least one exposure increment at the adjusted image exposure time.

2. The system of claim 1, wherein the VFL-projected light source comprises at least one light generator and a collimating lens, and is configured to provide VFL-projected light that is at least approximately collimated along the focus monitoring light path to the back side of the VFL lens.

3. The system of claim 2, wherein the VFL-projected light source is configured to contribute to the image light, wherein:
   the focus monitoring light path includes a beamsplitter located in the focus monitoring light path and in an imaging optical path between the back side of the VFL lens and the camera;
   VFL-projected light is input to the beamsplitter along the focus monitoring light path and output from the beamsplitter to the back side of the VFL lens, and through the VFL lens and the objective lens to illuminate the workpiece surface region; and
   the reflected VFL-projected light is reflected from the workpiece surface region and back through the objective lens and back through the VFL lens to the beamsplitter, where part of the reflected VFL-projected light is directed back along the focus monitoring light path, and part of the reflected VFL-projected light is directed as image light along the imaging optical path to the camera.

4. The system of claim 3, wherein the VFL-projected light source includes only one light generator that generates the VFL-projected light.

5. The system of claim 3, wherein:
   the VFL-projected light source comprises a first light generator that outputs light having a first wavelength range;
   the VFL-projected light source comprises a second light generator that contributes to the image light and outputs wavelengths outside the first wavelength range; and
   the imaging system further comprises a wavelength filter arranged between the camera and the VFL lens and configured to prevent light in the first wavelength range from reaching the camera.

6. The system of claim 1, wherein the optical detector comprises at least one of a wavefront sensor, a wavefront curvature detector, and a Shack-Hartmann sensor.

7. The system of claim 1, wherein:
   the VFL-projected light source is configured to provide the VFL-projected light during a focus determination time period, and the focus determining portion is configured to input the reflected VFL-projected light and output the at least one focus deviation signal during the focus determination time period; and
   the system is configured to acquire the at least one exposure increment at the adjusted image exposure time during an image acquisition time period that does not overlap with presence of the VFL-projected light during the focus determination time period.

8. The system of claim 1, wherein:
   the VFL-projected light source comprises a first light generator that outputs visible or invisible light having a first wavelength range;
   the image light comprises wavelengths outside the first wavelength range;
   the VFL-projected light source is configured to provide VFL-projected light having the first wavelength range continuously at least during a focus determination time period, and the focus determining portion is configured to input reflected VFL-projected light comprising the first wavelength range and output the at least one focus deviation signal continuously at least during the focus determination time period;
   the system is configured to acquire the at least one exposure increment at the adjusted image exposure time during an image acquisition time period that overlaps with presence of the VFL-projected light having the first wavelength range; and
   the imaging system further comprises a wavelength filter arranged between the camera and the VFL lens and configured to prevent light in the first wavelength range from reaching the camera.

9. The system of claim 8, wherein the system comprises an image light source that is located outside the VFL-projected light source and that is configured to illuminate the workpiece surface, and that includes an image light generator that provides the image light comprising wavelengths outside the first wavelength range.

10. The system of claim 8, wherein:
the VFL-projected light source comprises a second light generator that is an image light generator that outputs the image light comprising the wavelengths outside the first wavelength range, and a collimating lens; and
the image light is output through the collimating lens as VFL-projected light that is at least approximately collimated along the focus monitoring light path to the back side of the VFL lens and through the VFL lens to illuminate the workpiece surface.

11. The system of claim 1, wherein the adjusted image exposure time defines a particular phase timing relative to the periodically modulated focus position, and the system is configured to provide a focused image comprising a plurality of exposure increments at that particular phase timing during a plurality of periods of the periodically modulated focus position.

12. The system of claim 1, wherein the camera comprises a fast electronic shutter and the exposure strobe time controller is configured to control a shutter strobe timing of the fast electronic shutter to enable the at least one exposure increment at the adjusted image exposure time.

13. The system of claim 1, wherein the system comprises a strobed image light source that provides the image light, and the exposure strobe time controller is configured to control an image light strobe timing of the strobed image light source to enable the at least one exposure increment at the adjusted image exposure time.

14. The system of claim 1, wherein:
the VFL-projected light source comprises a first light generator;
the system comprises a focus determination light control circuit configured to control a focus strobe timing of the first light generator to provide at least one instance of strobed VFL-projected light having an initial phase timing relative to the periodically modulated focus position, at least during a focus determination time period; and
the focus determining portion is configured to input reflected strobed VFL-projected light having the initial phase timing and output a corresponding current focus deviation signal.

15. The system of claim 14, wherein the exposure timing adjustment circuit comprises the focus determination light control circuit, and the system is configured to perform a phase timing search that identifies a focus phase timing that produces a focus deviation signal corresponding to the strobed VFL-projected light being focused on the workpiece surface, wherein:
the focus determination light control circuit is furthermore configured to input a current focus deviation signal and automatically adjust the focus strobe timing to provide at least one instance of strobed VFL-projected light having an adjusted phase timing based on the current focus deviation signal;
the focus determining portion is configured to input reflected strobed VFL-projected light having the adjusted phase timing and output a corresponding current focus deviation signal;
the focus determination light control circuit and the focus determining portion are configured to operate iteratively, and the exposure timing adjustment circuit comprises a circuit configured to determine when a current focus deviation signal corresponds to the strobed VFL-projected light being focused on the workpiece surface, indicating that the corresponding adjusted focus strobe timing provides a focused phase timing;
the exposure timing adjustment circuit is configured to output an exposure timing adjustment signal that is indicative of the focused phase timing; and
the exposure strobe time controller is configured to input the exposure timing adjustment signal and automatically provide an adjusted image exposure time that corresponds to the focused phase timing.

16. The system of claim 15, wherein the focus determination light control circuit, the focus determining portion, the exposure timing adjustment circuit and the exposure strobe time controller are configured to operate iteratively, and the system is configured to iteratively provide a sequence of adjusted image exposure times that correspond to a sequence of focused phase timings while scanning across a workpiece surface, and provide a corresponding sequence of focused images while scanning across the workpiece surface.

17. The system of claim 1, wherein:
the VFL-projected light source is configured to provide the VFL-projected light during a focus determination time period, and the focus determining portion is configured to input the reflected VFL-projected light and output the at least one focus deviation signal during the focus determination time period; and
the system is configured to acquire the at least one exposure increment at the adjusted image exposure time during an image acquisition time period that does not overlap with presence of the VFL-projected light during the focus determination time period.

18. The system of claim 1, wherein:
the VFL lens is periodically modulated at a frequency of at least 3 kHz; and
the optical detector comprises a photodetector having a response time that is shorter than a period of the periodic modulation.

19. The system of claim 1, wherein:
the VFL lens is periodically modulated at a frequency of at least 3 kHz;
and the system comprises a focus determination light control circuit configured to control a focus strobe timing of a first light generator included in the VFL-projected light source, to provide at least one instance of strobed VFL-projected light having a defined phase timing relative to the periodically modulated focus position, at least during a focus determination time period; and
the optical detector comprises a photodetector having a response time that is longer than a period of the periodic modulation, and is configured to input reflected VFL-projected light having the defined phase timing to the photodetector.

20. The system of claim 19, wherein the VFL lens is periodically modulated at a frequency of at least 70 kHz.